United States Patent
Lande

(10) Patent No.: US 9,039,646 B2
(45) Date of Patent: May 26, 2015

(54) CHRONIC ACCESS SYSTEM FOR EXTRACORPOREAL TREATMENT OF BLOOD INCLUDING A CONTINUOUSLY WEARABLE HEMODIALYZER

(71) Applicant: Arnold J. Lande, Northport, MI (US)

(72) Inventor: Arnold J. Lande, Northport, MI (US)

(*) Notice: Subject to any disclaimer, the term of this patent is extended or adjusted under 35 U.S.C. 154(b) by 0 days.

(21) Appl. No.: 14/165,983

(22) Filed: Jan. 28, 2014

(65) Prior Publication Data

US 2014/0194804 A1 Jul. 10, 2014

Related U.S. Application Data

(62) Division of application No. 13/325,445, filed on Dec. 14, 2011, now abandoned, and a division of application No. 12/448,178, filed as application No. PCT/US2007/025864 on Dec. 19, 2007, now Pat. No. 8,109,893.

(60) Provisional application No. 60/875,633, filed on Dec. 19, 2006.

(51) Int. Cl.
*A61M 37/00* (2006.01)
*A61M 1/36* (2006.01)
*A61M 1/16* (2006.01)

(52) U.S. Cl.
CPC ............ *A61M 1/3661* (2014.02); *A61M 1/3655* (2013.01); *A61M 1/16* (2013.01); *A61M 1/1696* (2013.01); *A61M 1/3672* (2013.01); *A61M 2205/123* (2013.01); *A61M 2205/126* (2013.01); *A61M 2205/8206* (2013.01); *A61M 2209/088* (2013.01)

(58) Field of Classification Search
USPC ........... 604/4.01, 5.01, 5.04, 6.09, 6.11, 6.06, 604/6.07, 27, 30
See application file for complete search history.

(56) References Cited

U.S. PATENT DOCUMENTS

| | | | |
|---|---|---|---|
| 3,625,210 A | 12/1971 | Mikkelson |
| 3,864,259 A | 2/1975 | Newhart |
| 3,884,808 A | 5/1975 | Scott |
| 4,212,738 A | 7/1980 | Henne |

(Continued)

OTHER PUBLICATIONS

N Engl J Med. Nov. 17, 1966;275(20)1089-92. Chronic hemodialysis using venipuncture and a surgically created arteriovenous fistula. Brescia MJ, Cimino JE, Appel K, Hurwich BJ.*

(Continued)

*Primary Examiner* — Leslie Deak
(74) *Attorney, Agent, or Firm* — Nikolai & Mersereau, P.A.; Thomas J. Nikolai

(57) ABSTRACT

A patient wearable, continuously operating extracorporeal pump apparatus which accesses the patient's arterial venous pressure differential by applying external pressure to a subcutaneous graft that has been cannualized to modulate blood flow through an extracorporeal circuit and to drive the pump for delivering a medicament, such as an anticoagulant, to the site of an intravenous cannula to prevent clogging thereof and also to move a dialysate through a circuit, including a dialyzer and a dialysate rejuvenating cartridge, whereby kidney failure can be treated without recourse to prior art hemodialysis machines found in most treatment facilities. With slight modification, the present invention can be used to remove excess fluids from CHF patients, to remove toxins from the blood in those suffering from liver failure and to facilitate administration of insulin to diabetics and/or glucose to those having hypoglycemia.

1 Claim, 14 Drawing Sheets

(56) References Cited

U.S. PATENT DOCUMENTS

| | | | |
|---|---|---|---|
| 4,231,871 A | | 11/1980 | Lipps et al. |
| 4,235,231 A | | 11/1980 | Schindler et al. |
| 4,623,327 A | * | 11/1986 | Mahurkar .................. 604/6.16 |
| 4,623,450 A | | 11/1986 | Vantard et al. |
| 4,715,849 A | * | 12/1987 | Gion et al. .................. 604/540 |
| 5,284,470 A | | 2/1994 | Beltz |
| 5,863,421 A | | 1/1999 | Peter, Jr. et al. |
| 6,623,450 B1 | | 9/2003 | Dutta |
| 7,645,253 B2 | | 1/2010 | Gura et al. |
| 8,109,893 B2 | | 2/2012 | Lande |
| 2002/0103413 A1 | | 8/2002 | Bugge et al. |
| 2004/0186408 A1 | | 9/2004 | Behague et al. |
| 2005/0022422 A1 | | 2/2005 | Swigart et al. |
| 2005/0182349 A1 | | 8/2005 | Linde et al. |
| 2012/0095402 A1 | | 4/2012 | Lande |

OTHER PUBLICATIONS

Konner, Klaus. "The anastomosis of the arteriovenous fistula—common errors and their avoidance." Nephrol Dial Transplant (2002) 17:376-379.*

Arbios Systems, Inc., "The Key to Liver Support: Biological Liver Support Systems", May 21, 2005.

Beathard, Gerald A. et al., "Aggressive trademark of early fistula failure", Kidney International, May 22, 2003, U.S.

Brems, John J.; Brunson, Matthew; Salomon, Daniel R., "Extracorporeal Hepatic Support", CenterSpan, Recent Developments in Transplantation Medicine: Liver Transplantation, May 31, 2005.

Kimoto, Seiji, "The Artificial Liver: Experiments and Clinical Application", Professor of Surgery, The Department of Surgery, Tokyo University School of Medicine, pp. 102-112.

* cited by examiner

CHRONIC ACCESS SYSTEM FOR EXTRACORPOREAL TREATMENT OF BLOOD INCLUDING A CONTINUOUSLY WEARABLE HEMODIALYZER

CROSS-REFERENCE TO RELATED APPLICATION

This application is a Divisional application of application Ser. No. 13/325,445, filed Dec. 14, 2011, which is a Divisional application of application Ser. No. 12/448,178, filed Jun. 11, 2009, which is a 371 of PCT application serial no. PCT/US07/25864, filed Dec. 19, 2007, which claims benefit of U.S. Provisional Application Ser. No. 60/875,633, filed Dec. 19, 2006, the contents of each are hereby being incorporated by reference.

BACKGROUND OF THE INVENTION

I. Field of the Invention

This invention relates generally to artificial organs and in particular to a blood access system for the treatment of end stage kidney failure. The apparatus comprising a preferred embodiment includes a patient-wearable, extracorporeal system which accesses a patient's arterial/venous pressure differential and regulates the extracorporeal arteriovenous blood flow and proportionally with that blood flow, pumps and regulates dialysate flow in the case of hemodialysis (HD) for kidney failure. The externally wearable unit offers portable, continuous, HD for a patient. The HD unit of this invention also proportionally with the blood and dialysate, pumps and regulates anti-coagulant and CaMg additions.

II. Discussion of the Prior Art

Patients suffering from chronic end stage renal disease or acute traumatic kidney failure regularly undergo the process of HD in which chemical waste and water are removed from the blood using a system of semi-permeable membranes. Conventional chronic treatment requires the patient to remain sedentary for three sessions per week. Each treatment session constitutes approximately three to six hours at a treatment center or at home and additional hours for travel and recovery. It is an uncomfortable and tiring procedure, since patients must remain sedentary and because of the rapid rate at which their body fluids are adjusted toward normal. Approximately 100 times the usual daily intake of water, in the form of dialysate, passes by the artificial membranes opposite the blood during an average session. Consequently, failure of the dialysate preparation or membrane conduction systems may have severe consequences.

The process of HD becomes necessary when disease or trauma causes the kidneys to fail or become so impaired that they no longer adequately remove toxins and/or water from the blood. It involves mechanically and chemically assisted removal of toxins (largely urea) and water in a manner that restores a balance of fluids and electrolytes in the blood. The essential components for this process are a semi-permeable membrane and a dialysate solution that will absorb the unwanted blood components after they have passed through the membrane. A way of preventing clotting of blood in and around the dialyzer unit is required.

Interest in miniaturizing the equipment used in hemodialysis has resulted in the availability of small portable (as opposed to truly ambulatory) dialysis devices. Ash and Kessler in U.S. Pat. No. 4,071,444 provide an example of a portable dialysis machine.

As is pointed out in the Twardowski U.S. Pat. No. 5,336,165 there is a real need for equipment that will make at-home hemodialysis possible. There are nearly 500,000 patients on dialysis in the United States at any one time. Most of these patients must visit kidney dialysis centers three times a week and spend several hours on each of those days tied to a machine that includes an extracorporeal circuit for extracting blood, "cleaning" it, and returning it back into the patient. This not only exposes the patient or a third-party payer to very significant medical costs, but also adversely affects quality of life considerations. In an attempt to address this problem, Twardowski describes an at-home hemodialysis system that includes a dialyzer membrane and provision for passage of a dialysis solution along one side of the membrane and blood with uremia: components along the other side.

The Beltz U.S. Pat. No. 5,284,470 describes a portable, artificial kidney in the form of a self-contained unit whose size and shape is such that it is lightweight and relatively small so that it can be worn by the patient who is able to go about routine daily activities. The Beltz system includes a blood plasma separator unit, a chemical treatment unit, and a water removal unit. It also includes a cannula inserted in an arteriovenous shunt for gaining access to the patient's blood stream. The toxic whole blood is routed to the artificial kidney and then returned in detoxified form back to the patient. The artificial kidney includes a separator packet for extracting a predetermined amount of plasma from the patient's blood and then a further packet containing a treatment chemical for cleansing the plasma is included in the flow path. Means are provided to remove water from the plasma before the cleansed plasma is returned to the patient's body. Blood flow through the unit is due primarily to the hydrostatic blood pressure of the patient, but it is recognized that a lightweight pump and battery may be needed to generate additional pressure for routing the cleansed plasma back into the patient.

A continuous-use ambulatory hemodialysis unit is described in U.S. Pat. No. 3,864,259 of Newhart. It features a harness that secures a dialysate reservoir to the patient's hip and a perfusion unit on the anterior thigh, connected to a femoral shunt. The perfusion unit has multiple dialysis tubules bathed in dialysate, enabling the removal of waste products from the blood in the tubules. The apparatus consists of seven exterior parts: harness, diaphragm pump, reservoir, perfusion unit, dialysate exchange unit, and femoral arterial and venous cannulae. The exchanger is smaller than the perfusion unit at approximately 8.5 cm×6 cm and 1 cm deep. It should be apparent that this apparatus is cumbersome and uncomfortable.

OBJECTS

A principal object of the invention is to provide a new and improved apparatus for extracorporeal treatment of blood, including hemodialysis and hemofiltration in the form of a wearable unit. This wearable HD unit is more convenient than standard treatment, since it performs HD substantially continuously, 24 hours a day, 7 days a week, and largely eliminates the need for time-consuming, sedentary, hospital or clinic dialysis. The patients are also spared the alternative of having to endure liters of an ascites-like peritoneal dialysis solution in their abdominal cavity and needing to spend several hours each day carrying out the necessary fluid exchanges for CAPD.

A further object is to broaden applicability by utilizing a blood arterio/venous pressure differential powered pump design that offers mechanical advantage due to the lever arm principle. This particular pump design has broad application as an extracorporeal blood treatment system, independent of the hemodialyzer component.

Yet another important object of the invention is to provide an apparatus that nearly continuously accesses A/V pressure differential by interchangeably applying external pressure over a subcutaneous plastic fistula graft or an in situ debranched arteriovenous fistula segment, at two separate sites so as to avoid tissue necrosis.

A still further object of the present invention is to provide a patient-wearable hemodialysis and/or hemofiltration system which is miniaturized such that it is wearable without discomfort and conveniently situated on a patient's limb, as on the wrist and forearm.

SUMMARY OF THE INVENTION

The present invention comprises a blood dialysis apparatus for ambulatory patients so that substantially continuous removal of urea, water, salts and other waste products from the patient's blood stream is accomplished. Supplementary accelerated hemofiltration can also be accomplished at night in a recumbent setting by applying suction around a collection bag. The device comprises a pair of superposed flexible cuffs adapted to be wrapped about and secured to a limb of a patient, each cuff comprising first and second superposed sheets of plastic film selectively bonded to one another to define a plurality of isolated fluid flow paths including, but not limited to, a blood circuit, a dialysate circuit, an anti-coagulant administrative path and a calcium-magnesium (CaMg) introduction path.

Enclosed in the cuff is a liquid impervious chamber containing a plurality of hollow, tubular dialysis/hemofiltration fibers. The chamber is connected in the blood circuit and the dialysate circuit such that blood can flow through the lumens of the tubular dialyzer fibers from an inlet end to an outlet end thereof while dialysate flows about the exterior of the dialysis fibers within the chamber. Alternatively, the chamber can be arranged so that the dialysate flows through the lumens and the blood over the fiber exteriors. The cuff also temporarily supports one or more parallel-chambered dialysate toxins adsorbing cartridges.

A first cannula is used to access arterial blood that is coupled through the blood circuit to an inlet end of the tubular dialyzer fibers and a venous cannula is coupled to the outlet end of those dialyzer fibers. The anti-coagulant administration path preferably includes a first compressible reservoir for containing a quantity of a liquid anti-coagulant drug. Likewise, the CaMg path includes a flexible compressible chamber for containing a solution of calcium and magnesium ions.

A specially designed pump arrangement is provided that is adapted to be actuated by blood flow through the blood circuit to force proportionally metered quantities of anti-coagulant drug from the first compressible reservoir to a location near the inside of the tip of the arterial cannula and a proportionally metered quantity of CaMg solution from the second compressible reservoir into the dialysate inlet to the dialyzer.

In accordance with the operation, the pump arrangement may comprise a first roller cage disposed over one of the first and second disposables and overlying a portion of first anti-coagulant and first CaMg paths and a second roller cage disposed over a second of the first and second RF sealed disposables, overlying portions of the second anticoagulant and the second CaMg paths. The roller cages are adapted to be rotated by a wedge-shaped lever and a ratchet pawl that is actuated by the flow of the patient's blood due to the arterial/venous pressure differential and when cooperating with the flexible flow paths, acts as a peristaltic pump for delivery of the anticoagulant and the CaMg solution.

Basic to the concept is the method for obtaining access to arterial and venous pressures, chronically, by biweekly inserting small catheters into plastic fistula grafts or a debranched venous equivalent, both proximal and distal to reciprocal compression sites. Also basic to the concept is how control of the rate of extracorporeal blood flow is exercised, how a dialysate flow rate proportional and approximately equal to the blood flow is maintained and how proportional control over the rate of the pump delivering the anticoagulant and CaMg supplements is maintained. All of these are accomplished by a swinging lever mechanism whose displacement is based on controlled blood flow in and out of expandable ventricles in the disposable cuff's blood circuit. The lever serves to appropriately limit and define blood flow and to transfer power from the blood to the dialysate, anticoagulant, and CaMg delivery functions.

DESCRIPTION OF THE DRAWINGS

The foregoing features, objects and advantages of the invention will become apparent to those skilled in the art from the following detailed description of preferred embodiment, especially when considered in conjunction with the accompanying drawings in which like numerals in the several views refer to corresponding parts.

DESCRIPTION OF THE PREFERRED EMBODIMENT

Figure 1:
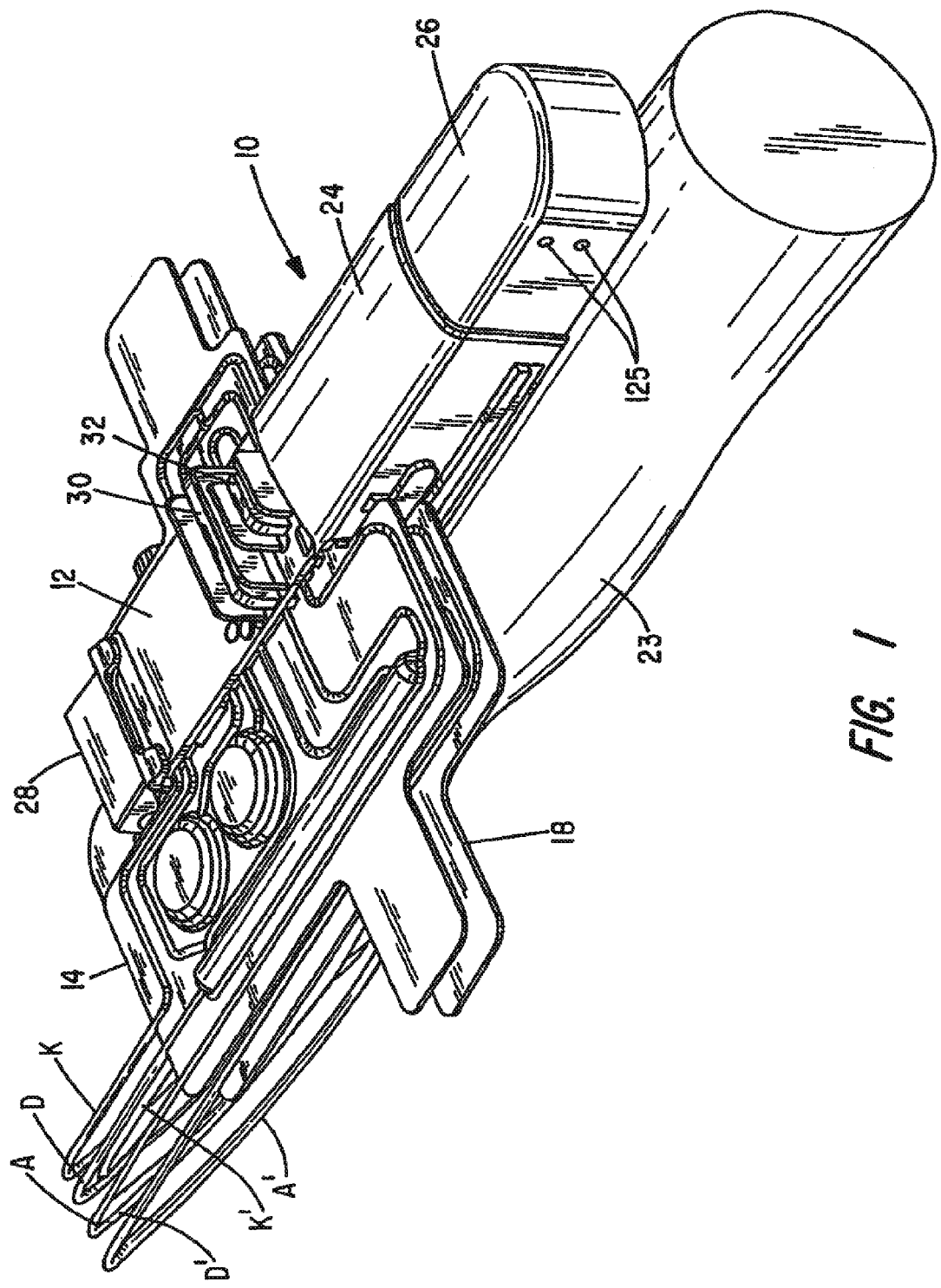
FIG. 1 is a perspective view of the wearable hemodialyzer constructed in accordance with a preferred embodiment of the present invention.

Certain terminology will be used in the following description for convenience in reference only and will not be limiting. The words "upwardly", "downwardly", "rightwardly"

and "leftwardly" will refer to directions in the drawings to which reference is made. The words "inwardly" and "outwardly" will refer to directions toward and away from, respectively, the geometric center of the device and associated parts thereof. Said terminology will include the words above specifically mentioned, derivatives thereof and words of similar import.

Figure 2:
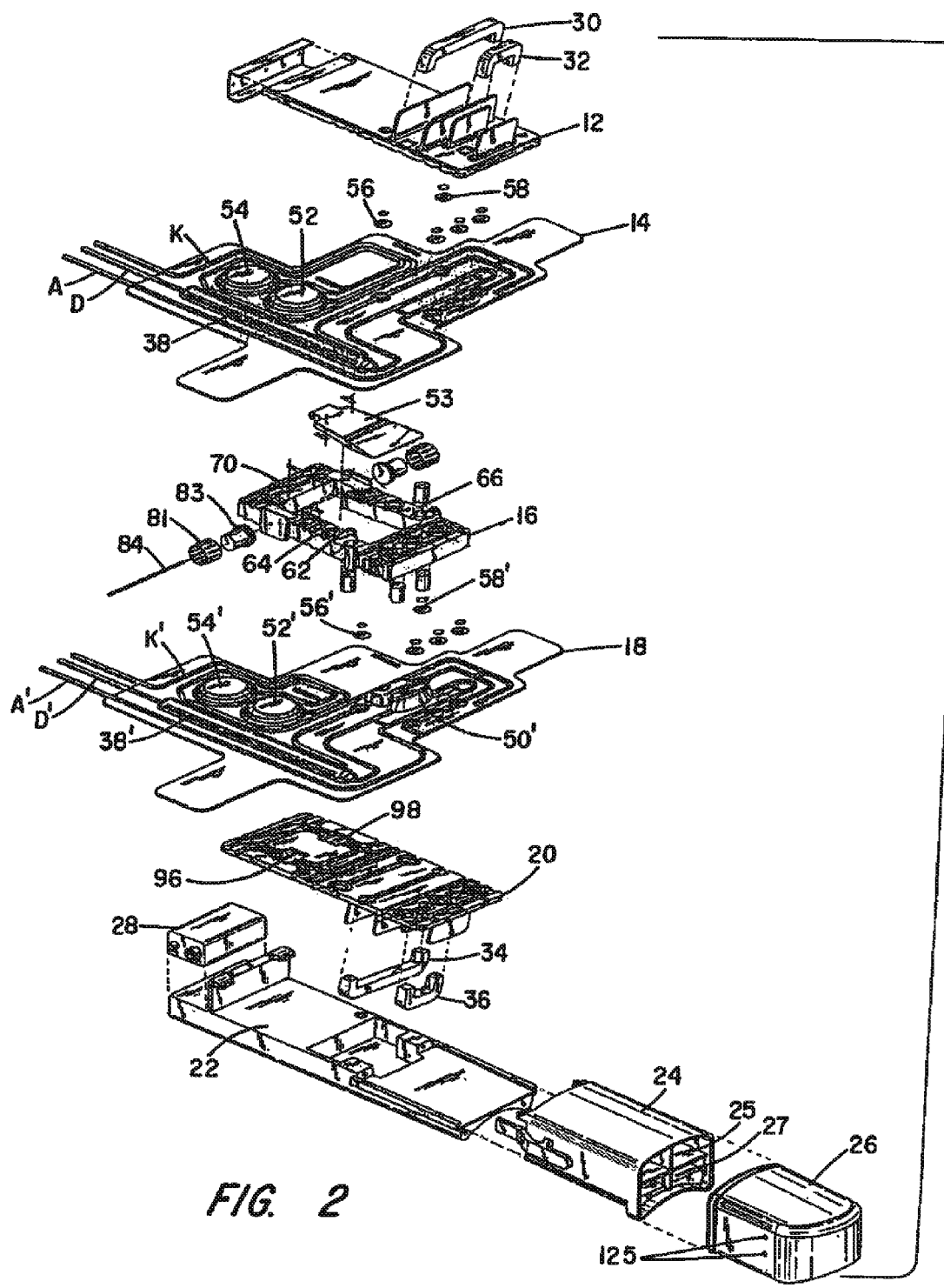
FIG. 2 is an exploded view of the wearable hemodialyzer of FIG. 1.

Referring to FIG. 1 and the exploded view of FIG. 2, there is indicated generally by numeral 10 a preferred embodiment of the invention, namely, a portable, wearable, hemodialyzer. It is seen to comprise a layered construction of a rigid non-disposable top end plate 12, an upper, flexible, blood contacting plastic disposable member 14, a non-disposable, rigid molded-plastic pump frame 16, a lower, disposable, plastic, blood-contacting member 18 and a non-disposable bottom end plate 20. The aforementioned components are adapted to be mounted onto a rigid, non-disposable base plate member 22 to which a replaceable dialysate-restoring cartridge members 24 and 26 is also adapted to be removably affixed in a manner that will be more particularly described herein below. A battery 28 is also removably clamped to the base plate 22 and is used to power an electronic timing control circuit (FIG. 10) and electromagnets 30, 32 that are affixed to the top plate 12 and electromagnets 34 and 36 that mount to the underside of the lower bottom end plate 20.

Figure 8:
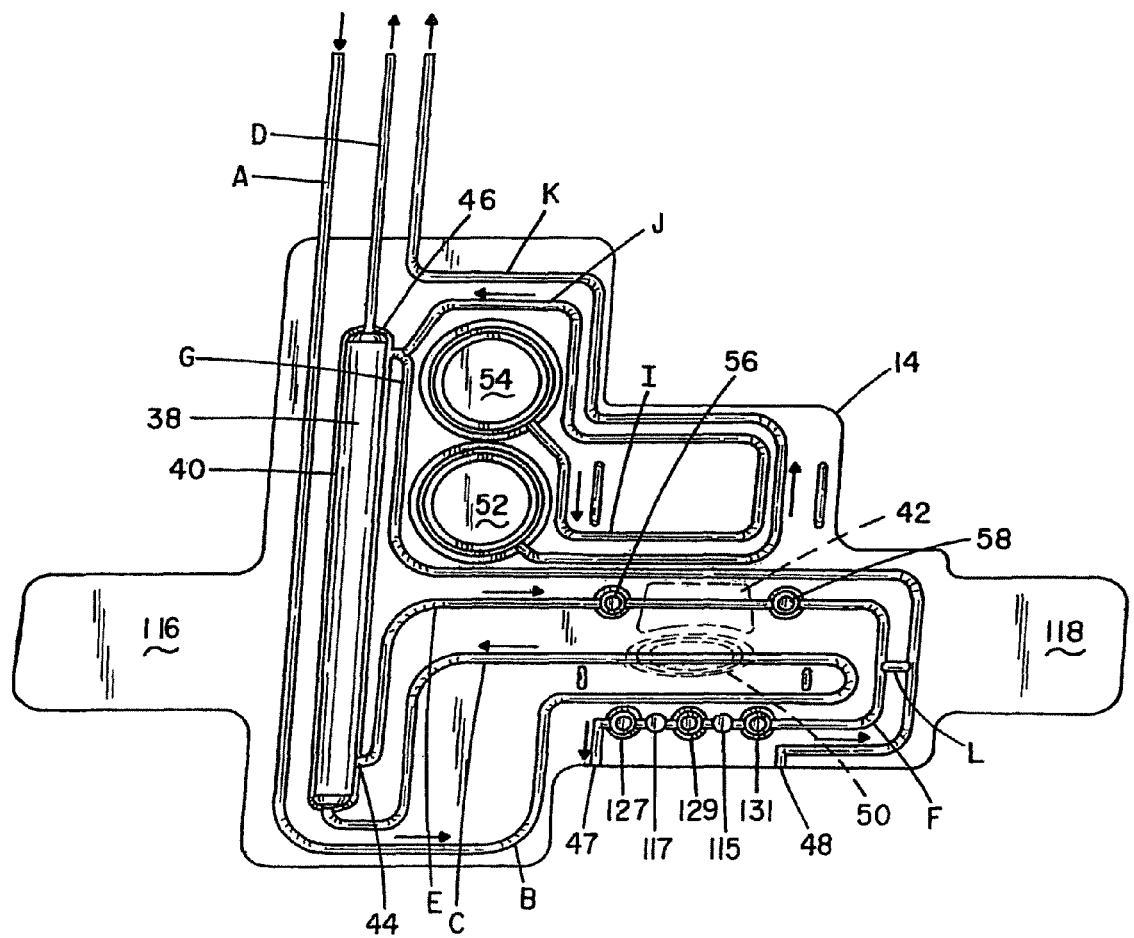
FIG. 8 is a plan view of the upper disposable blood contacting layer.

Concentrating first on the upper disposable, plastic, blood-contacting member 14 that is more particularly illustrated in the plan view of FIG. 8, it is seen to comprise first and second flexible plastic sheets that are RF welded or otherwise bonded together in a predetermined pattern so as to form a plurality of sealed, isolated, chambers and ventricles and fluid flow paths there between. The fluid flow paths include a recirculating blood circuit including tubular segments A, B and C leading through a blood ventricle 50 and tubular segment E to a blood input end of a dialyzer member 38 (FIG. 8). The dialyzer member 38 preferably consists of a tubular outer casing 40 that is sealed between the double layers of flexible plastic that are RF sealed to one another. The soft or hard casing 40 is fluid impermeable and contains within it a large plurality of hollow tubular dialysis fibers configured as a bundle. More particularly, the dialyzer 38 may be a miniature version of a commercially-available conventional, hollow fiber dialyzer and the hollow dialysis fibers used therein typically have an internal diameter of between 200 and 400 μm, allowing a high number of fibers to be contained within the tubular casing 40. The casing 40 may have an outside diameter of about ⅓ inch.

As is known in the art, the dialysis fibers comprise semi-permeable membranes, typically composed of cellulose or polymeric, directives. A pair of miniature dialyzers like that contemplated may, together, provide a generous total exchange surface of about 1000-1500 square centimeters (0.1-0.15 square meters). A suitable manifold of known construction is provided so that arterial blood flowing into the dialyzer 38, via the tubular branches A, B and C and the blood ventricle 50 in FIG. 8, is made to flow through the central lumens of the bundled tubular fibers in a first flow direction, while dialysate solution is made to flow in a predetermined direction, preferably the counter current direction, through the dialyzer casing 40 such that the outer surfaces of the tubular fibers are bathed effectively by the dialysis fluid.

Blood exits the dialyzer member 38 via a tubular path segment D defined between the superposed sheets of plastic comprising the upper disposable member 14. The manner in which a patient's blood is accessed will be described in greater detail herein below.

With continued reference to FIG. 8, the RF welded, laminated plastic sheets comprising the disposable member 14 further includes a dialysate circuit having a flexible compressible and expandable dialysate ventricle 42 that projects from the undersurface of the member 14 and is shown in phantom line in FIG. 8. This ventricle is in fluid communication with a tubular conduit comprising segment E leading from a dialysate outlet port 44 of the dialyzer and an inflow path of the dialysate rejuvenating cartridge ending at inlet port 47 of the cartridge and including auxiliary pumping valves 131, 129 and 127 and the two auxiliary pumping ventricles 117, 115 there between. Tubular segments H and G lead from an outlet port 48 of the dialysate rejuvenating cartridge 24/26 back to inlet port 46 of the dialyzer, completing the dialysate circuit. A recirculation circuit L may be opened when auxiliary dialysate pumps 117, 115, 131, 129, 127 are employed, to avoid negative pressure.

Disposed in segment C of the blood path of the upper disposable member 14 on its undersurface is an expansible blood ventricle 50 which serves to displace a pump actuating lever 53 (FIGS. 2 and 9) in a manner to be explained in greater detail below. Also cooperating with the pump actuating lever 53 is the expansible dialysate bladder 42.

A reservoir 52 formed by selective welding of the sheets comprising disposable member 14 is configured to contain a suitable anti-coagulant, e.g., heparin, possibly guarded in a crushable ampule, and it is adapted to feed the anti-coagulant via tubing segment K to the bloodstream just proximate the interior of the tip of the arterial cannula (not shown) used to access the patient's circulatory system. As will be explained further herein below, the anti-coagulant is metered out from the reservoir by a peristaltic pump driven by the patient's own arterial/venous pressure differential and serves to prevent clotting of blood within the cannula needle entry and throughout the device, while avoiding undesirable systemic delivery of the anti-coagulant.

A bladder 54 formed in the upper disposable between its laminated sheets is adapted to contain a calcium magnesium (CaMg) solution, also possibly guarded in a crushable ampule, that is added to the cleansed dialysate via tubular segments I and J leading to the dialyzer dialysate inflow port 46.

As is explained in fuller detail below, the CaMg aqueous solution helps rejuvenate the dialysate solution after it passes through the toxin removing sorbent cartridge 24/26.

Connected in series with the dialysate ventricle 42 are passive check valves 56 and 58 which selectively open and close to permit emptying and filling of the dialysate ventricle as the pump lever 53 presses upon or retreats from its contact with ventricle 42.

Figure 7:
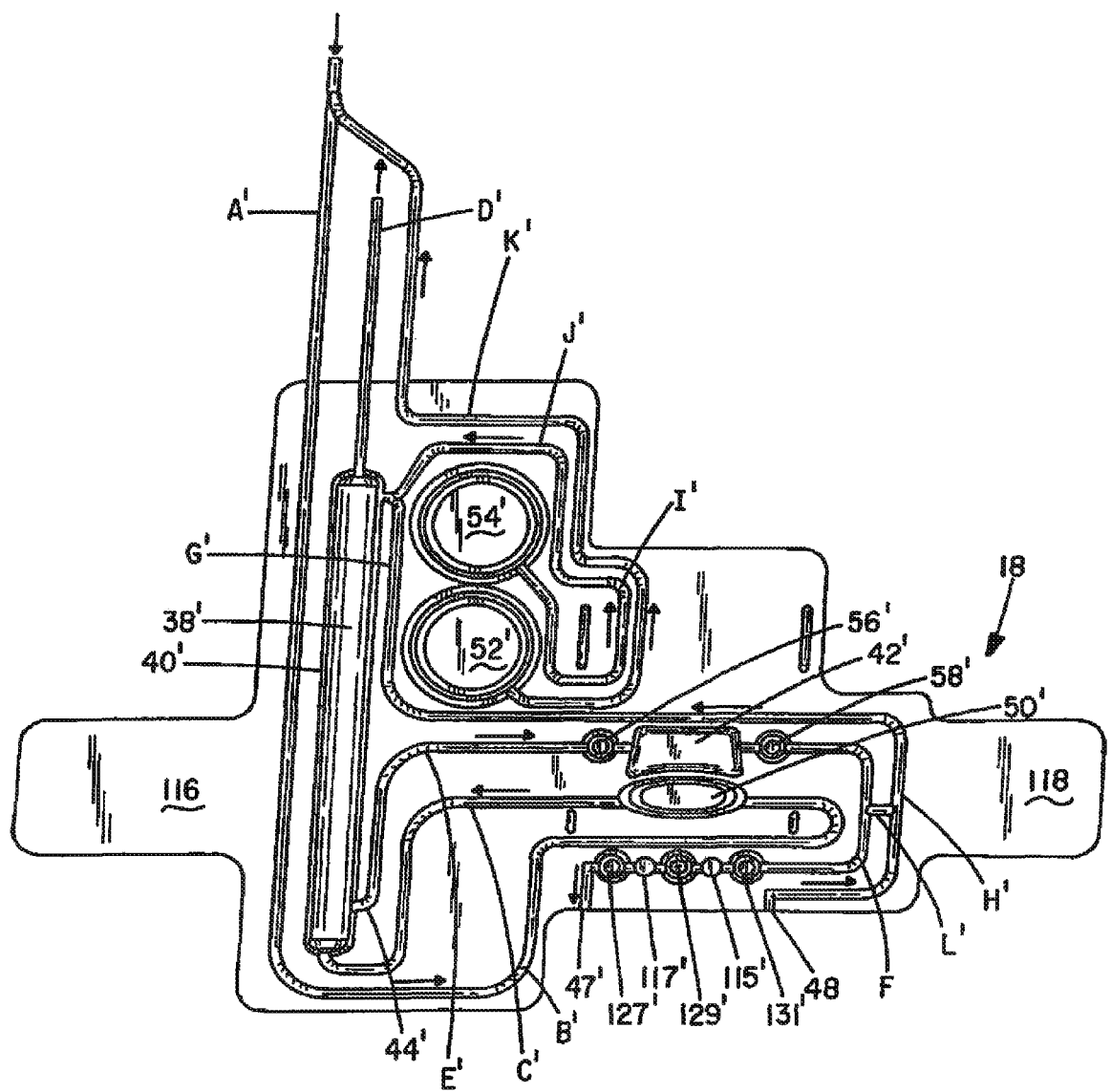
FIG. 7 is a plan view of the lower disposable blood contacting layer.

The lower disposable member 18 shown in FIGS. 1, 2 and 7 is a substantial duplicate of the upper cuff member 14. It includes a blood circuit containing a second dialyzer 38' and an expandable blood ventricle 50', connected by tubing to dialyzer 38' and to a venous cannula (not shown) connected to tubing segment D'. Lower disposable member 18 also includes a dialysate circuit, an anti-coagulant circuit path and a CaMg circuit path arranged to be functionally hut, in the case of the anti-coagulant and CaMg conduits, not precisely topographically congruent to the corresponding circuits on the disposable cuff member 14.

As seen in the exploded view of FIG. 2, disposed between the upper and lower cuff members 14 and 18 is a non-disposable pump frame member 16, which is preferably injection-molded from a suitable plastic. It is seen to comprise a generally rectangular block of a predetermined length, width and depth dimension that includes a centrally disposed somewhat rectangular opening 62 defined by left and right side members, 64 and 66, and front 68 and rear 70 end members.

Figure 9:
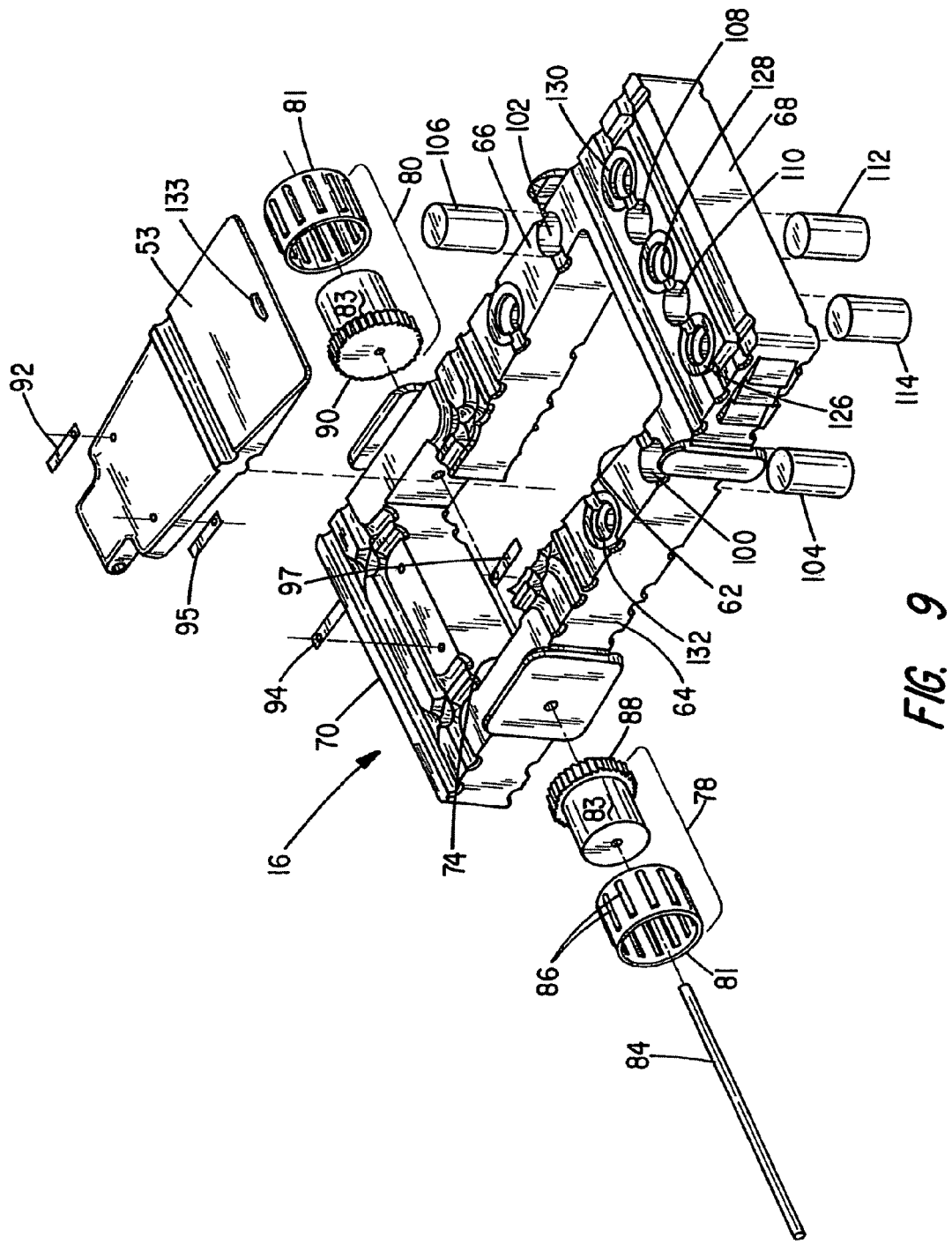
FIG. 9 is a detailed exploded view of the non-disposable pump frame subassembly used in the wearable hemodialyzer of the present invention.

Pivotally mounted within the central rectangular opening 62 is the swingable lever plate pump actuating lever 53. More particularly, and as can be seen in FIGS. 2 and 9, the frame member 16 includes left and right rectangular openings 74 and 76 and disposed within those openings are roller pump assemblies 78 and 80 that are journaled for rotation on shaft 84 which also serves to hingedly connect the swinging lever plate 53 to the opposed side edges 64 and 66 of the frame member 16. The conventional roller cages 78 and 80 each comprise a toroid of circular cross-section 81 that is formed from a metal or suitable plastic and which includes a plurality of regularly spaced axially extending grooves or slots in which are loosely retained wire-like rollers, as at 86, that extend across the width dimension of the roller cage 81. The rollers are driven to roll about high friction tape coated metal spools 83, but the rollers progress at only ½ the speed of the surface of the spools because the rollers rotate in the opposite direction from the rotation of the spools.

Secured to a side surface of the spools 83 are annular ratchet gears 88 and 90. Referring still to FIG. 9, there is shown mounted on the lever plate 53 and cooperating with the teeth on the ratchet gear 88 a rotation motivating pawl 95. Likewise, a reverse rotation-preventing pawl 94 is affixed to the end wall 70 of the frame 16 and is cantilevered so that its free end engages the ratchet teeth on the ratchet gear. With the described arrangement, as the lever plate 53 is made to pivot downward (clockwise) about the shaft 84, the associated spool 83 (ratchet 88) will be made to rotate in the same direction.

As the lever plate is made to pivot in the upward counter-clockwise direction when viewed in FIG. 9, the rotation motivating pawl 92 will engage the ratchet teeth on the spool associated with the roller cage assembly 80 to rotate that roller cage in a counterclockwise direction. Reverse rotation will be prevented by pawl 97 attached to frame end 70. The rollers 86, however, will rotate clockwise around their own axes.

As the rollers 86 rotate about the spools 83, they are pressed against RF sealed conduits disposed in the roller races 96 and 98 (FIG. 6) formed in the top and bottom plates 12 and 20 to effectively form peristaltic roller pumps for the anti-coagulant and CaMg and possibly other solutions. With continued reference to FIG. 9, first and second bores 100 and 102 are formed through the thickness dimensions of the frame plate side walls 64 and 66 and loosely fitted into these bores are conduit occluders 104 and 106 which may comprise cylindrically-shaped permanent magnets. The occluders are dimensioned to slide freely within their respective bores 100 and 102 under influence of electromagnets 30 and 34. Likewise, similar bores 108 and 110 are formed through the thickness dimensions of the frame pump end walls 68 and, again, slidable permanent magnet occluders 112 and 114 are insertable within the respective bores 108 and 110 to be acted upon by electromagnets 32 and 36 to function as pump bladder compressors for auxiliary dialysate pump ventricles 115 and 117 in FIG. 8.

Figure 6:
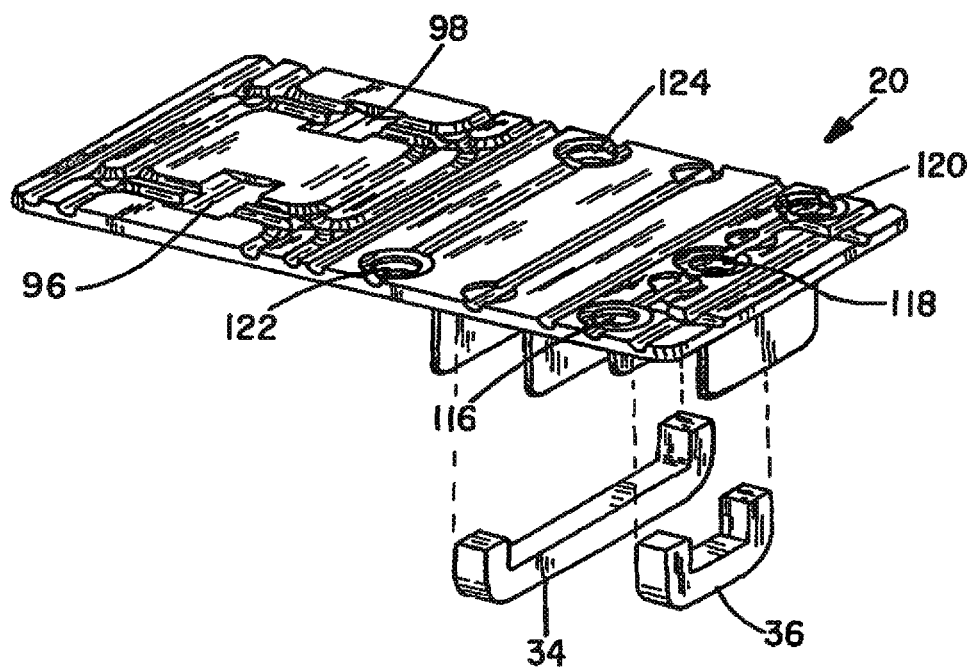
FIG. 6 is an enlarged perspective view of the bottom end plate which is substantially a replication of the top end plate.

Also formed in the upper and lower surfaces of the side walls 64 and 66 and front wall 68 and top and bottom end plates 12 and 20 are somewhat circular depressions as at 116-124 in FIG. 6 which are aligned with similar recesses 126-134 on frame member 16 in FIG. 9 and complementary recesses on the underside of top plate 12 when assembled as shown in FIG. 1. These recesses contain passive check valves (poppet or flap), as at 56 and 58, in FIGS. 8 and 56' and 58' in FIG. 7. Poppets 56', 58', 56, 58 are seen in FIG. 2. Referring again to FIG. 2, the frame member 16 is sandwiched between the upper and lower disposable cuff members 14 and 18 such that the blood ventricles 50 and 50 are positioned on opposite sides of the lever plate 53 and displaced a predetermined distance from the axis of the shaft 84 and of the roller cages 81. Similarly, the dialysate ventricles 42 and 42' are also on opposite sides of the lever plate 53. Even though the dialysate conduits are shown as positioned closer to the fulcrum 84 of lever 53, the dialysate ventricles might be placed at an equal or greater distance from the fulcrum than the blood bladders by curving the conduits or by displacing the centers of the dialysate ventricles, nearer to the thinner edge of the lever plate. This would make it even more unlikely for a higher pressure to be generated in the dialysate circuit compared with that in the driving blood circuit, further preventing dialysate from entering the bloodstream.

The tubular passageways leading from the anticoagulant reservoirs 52 and 52' and the CaMg reservoirs 54 and 54' are located to cooperate with pump assemblies 78 and 80 so as to function as peristaltic roller pumps. That is to say, as the roller pumps 78 and 80 are driven by the pivoting action of the lever plate 53 in the manner already described, the rollers force measured proportional quantities of an anti-coagulant and CaMg solution from their respective reservoirs 52, 52' and 54, 54' and along conduits leading to the arterial cannula or in to the cleansed dialysate conduits.

The permanent magnets occluders 104 and 106 serve as conduit occluders and function to open and close the lumens of the blood flow circuit C and C' to allow the arterial/venous pressure differential to alternatively fill and empty the blood pump ventricles 50 and 50' under influence of electromagnets 30 and 34 carried by the upper and lower end plates 12 and 20. As will be later explained, the electromagnets are operated in time phase and spatial polarity oriented equality, both North poles to the left and both South poles to the right, or visa versa. That is to say, when electromagnets 30-34 are pulsed, they function to cooperatively, directionally, attract and repel the North and South poles of each permanent magnet 104 and 106 to cooperatively move the conduit occluder upward or downward. The two conduit occluder permanent magnets' poles being identically oriented and under the influence of the opposite ends of the identically oriented electromagnets, the permanent magnets are moved in opposite directions in order to position them to block the flow of blood into the first bladder 50 and out of the second 50'.

Subsequently, with current reversal, the permanent magnets occluders 104 and 106 are attracted and repelled in the opposite directions with regard to near contact with the corresponding points on the others of the four blood conduits, blocking the flow of blood out of the first bladder 50 and into the second 50'.

Small, linear plastic knife edges (not shown) may be affixed to the RF sealed disposable precisely over the conduits that are meant to be occluded for blood cycling function. Affixing knife edges to the disposable is superior to having them be part of the permanent magnet occluders because positioning is thereby perfect every time and not dependent on positioning of the whole RF disposable between the frame 16 and the upper and lower end plates.

The wrist and forearm-wearable artificial kidney, as depicted in FIG. 1, is sufficiently small and light in weight to be unobtrusively worn 24 hours a day, 168 hours a week. VELCRO fasteners on the laterally projecting tabs 116 and 118 of the blood-contacting disposables of FIGS. 7 and 8 help to hold the device firmly in place on the forearm and wrist of the patient. It is also contemplated that a custom-molded porous foam "second skin" may be disposed between the base member 22 and the wearer's forearm to provide increased comfort and to assure that the graft compressors fastened to the second skin will remain precisely positioned over the subcutaneous graft.

The disposable cuffs 14 and 18 are sealed while there is some air pressure within or suction without, to assure that the sealed in ducts conduits tend toward having open circular lumens and do not collapse and stick together, plastic sheet to plastic sheet, when not distended by a contained liquid.

The device of the present invention operates to meter-modulate blood flow at a certain rate which automatically coordinates proportionally with the heparin anticoagulant administration, a heparin administration that is plentiful for preventing clotting within the device, but insufficient to result in systemic (total body) anticoagulation. Desirable prophylactic anticoagulation of the body does result.

Blood cleansing requirements must be considered as well. About 20-30 ml/min of blood flow through the device, 168 hours a week, will serve generously for the dialysis task. Dialysate is not only being modulated, but also pumped, secondarily, by the blood pressure differential. In this case, there is a proportional, approximately equal, countercurrent blood and dialysate flow. Proportionality also applies to added CaMg, which is required to reconstitute these two substances that have been completely stripped from the dialysate during one pass through the adsorbent cartridge. Since it is all gone, it can be wholly, proportionally, replaced into the dialysate flow with confidence.

Potassium is also stripped from the dialysate by the adsorbent cartridge 24/26 but it usually exists in excess, or at least in abundance, in uremic and other severely challenged patients. So, depending on lab findings, K+ may be aggressively removed by adding no potassium in to the dialysate, it might be drawn down slowly by including a normal small amount of K+ in the dialysate or it might actually be replaced if too much has been removed. It is anticipated that the very safe second option will be utilized most often in chronic, non-traumatic patients who will thus remain within normal limits without much manipulation. In the system we are describing, there is of course no exogenous dialysate replacement and cartridges with different K+ scrubbing capabilities will be utilized per the physician's prescription.

The inflow and outflow of dialysate from its pump ventricles can be directed either by one-way passive check valves that are located in the dialysate circuits at a physical position wherein the check valves will reside in the depressions 126-134 (FIG. 9) on the upper and lower surfaces of the frame member 16, or alternatively, active magnetic valves, as described for the blood circuits, may be so located. The check valve locations on the upper disposable cuff member 14 and associated with the dialysate circuit are identified by numerals 56, 58, 127, 129 and 131 that determine the allowed direction of flow of liquid through the respective circuits. Passive check valves may consist of thin washers with either poppets or flaps situated to permit flow in only the desired direction. The washers are RF sealed and compressed within the disposable and the conduit grooves are inscribed in the hardware to allow the fluid to approach the hole in the washer only on one side and to depart the hole only on the other.

The direction of flow of the DC current supplied by battery 28, hence the polarity of the horizontal electromagnets 30 and 34 should be reversed about every 5-15 seconds. Preferably located near the apex (tip) or side of the lever plate 53 is a small permanent magnet 133 (FIG. 9) which cooperates with a Hall sensor (or a bi-directional, current reversing reed switch mounted in the front member 68 or side member of the pump frame plate 16. As the magnet 133 sweeps past the Hall sensor, it causes the Hall sensor to reverse the direction of the next upcoming electrical trigger signal to an electronic circuit of FIG. 10, which functions to drive the electromagnets 30-34 at predetermined time intervals.

Figure 10:
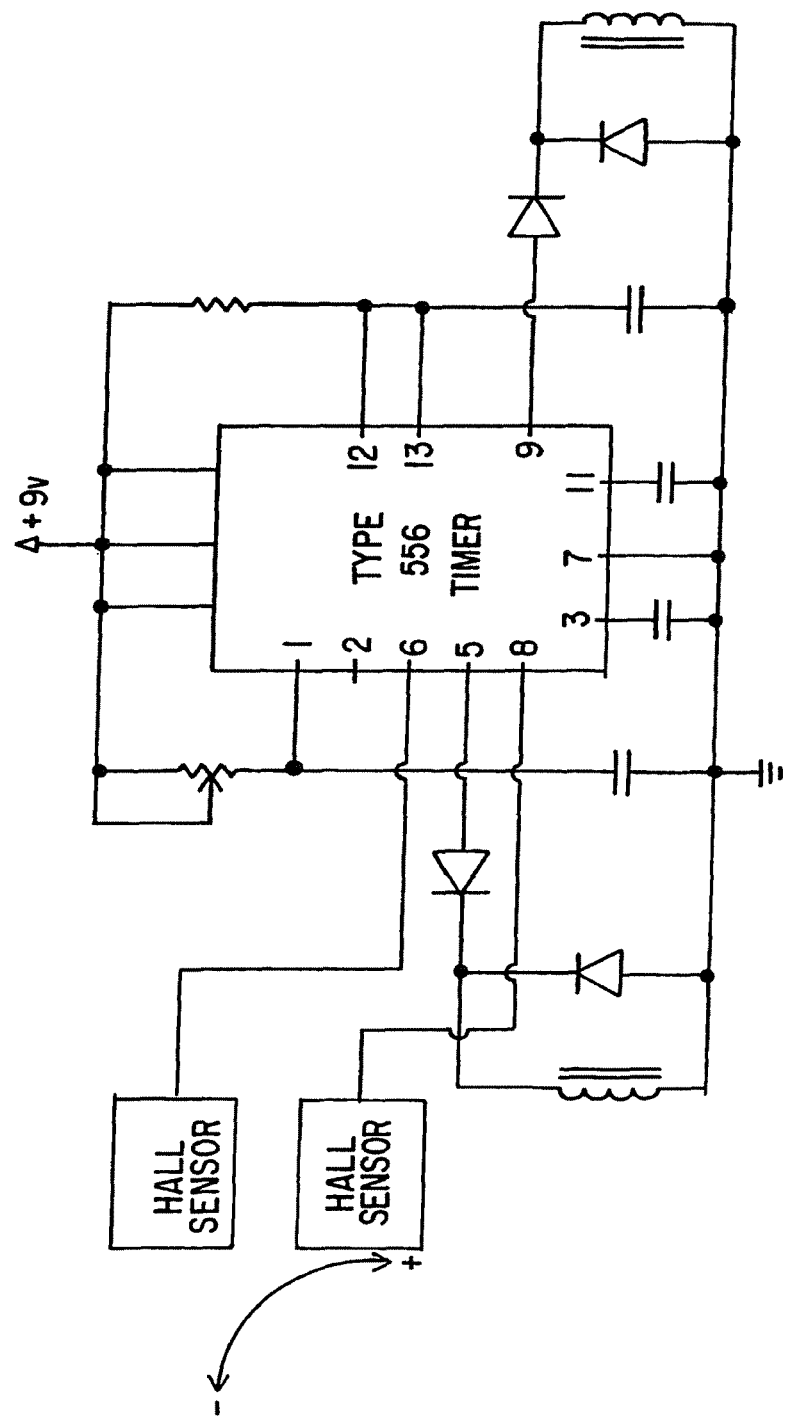
FIG. 10 is an electrical schematic diagram of a polarity reversing, circuit employed.

Referring to FIG. 10, the electronic circuit is powered by a battery 28 and may preferably comprise a Type 556 dual-timer integrated circuit chip that when triggered by an input signal on pin 6 thereof causes an output signal at pin 5 that will energize the electromagnets at a predetermined time, e.g., every 5-15 seconds. Later on, after the lever plate 53 carrying the magnet 133 has swept past the Hall sensor and reversed the circuitry, a trigger input will be applied to pin 8 of the Type 556 IC chip, now causing an output current at pin 9 to flow through the electromagnets 30 and 34 to energize them for a predetermined brief period of time established by the RC timing elements employed. As already mentioned, the permanent magnets 104 and 106 are attracted in opposite directions spatially against electromagnets 30 or 34, depending upon the relations between the alternating poles of the electromagnets and the permanent poles of the permanent magnets. As will be seen subsequently, electromagnets 32 and 36 are programmed identically, but timed differently to perform two stage, rapid pulse auxiliary pumping of the dialysate through the cartridge 24/26 utilizing permanent magnets 112, 114 in cylindrical bores 108, 110 to alternately compress ventricles sealed between valves 127, 129, 131 and 127', 129' and 131' in the RF sealed disposables of FIGS. 7 and 8.

Figure 4:
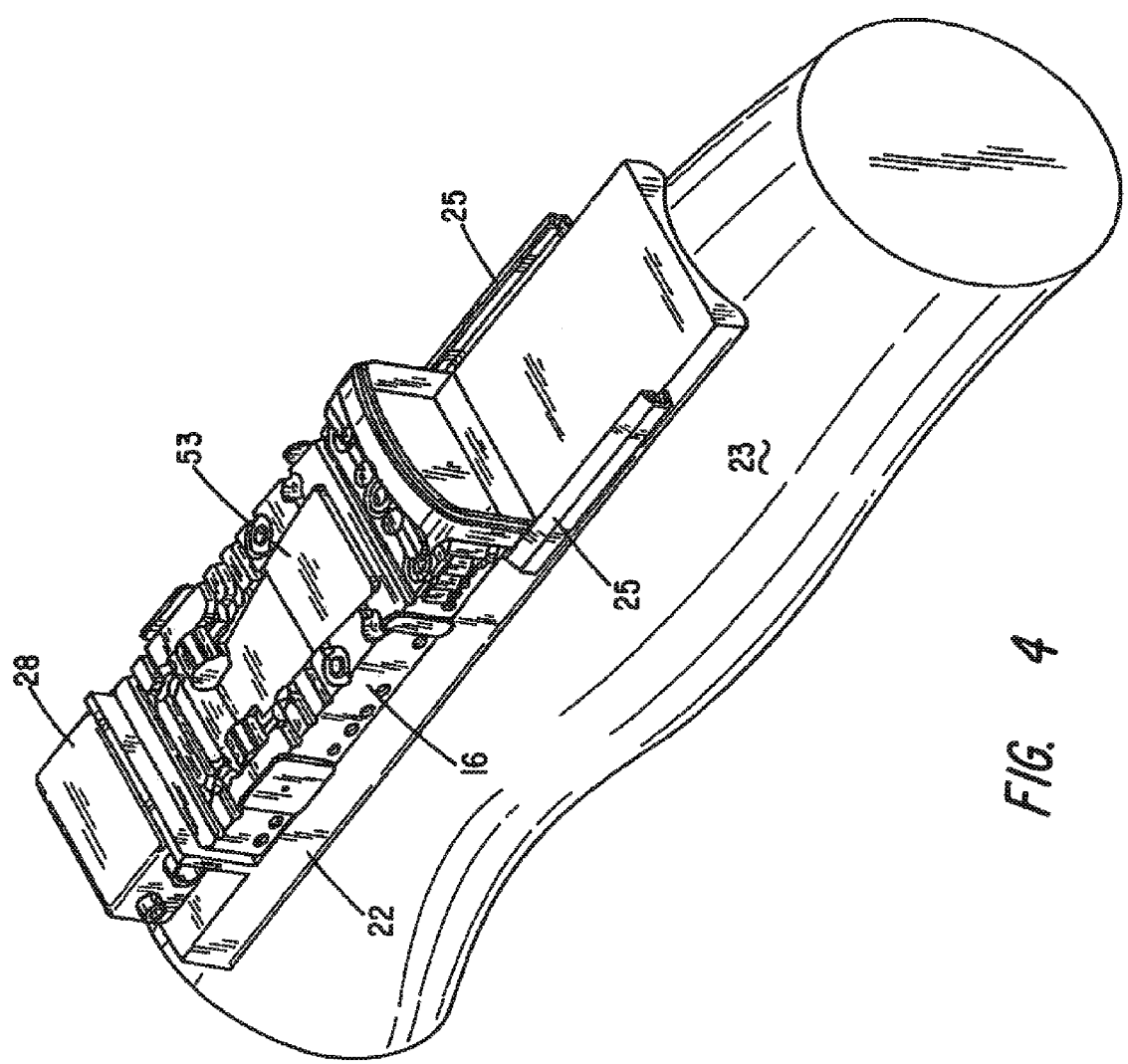
FIG. 4 is a perspective view of the non-disposable part of the device of FIG. 1, but with top end plate and part of the cartridge assembly removed.
Figure 5:
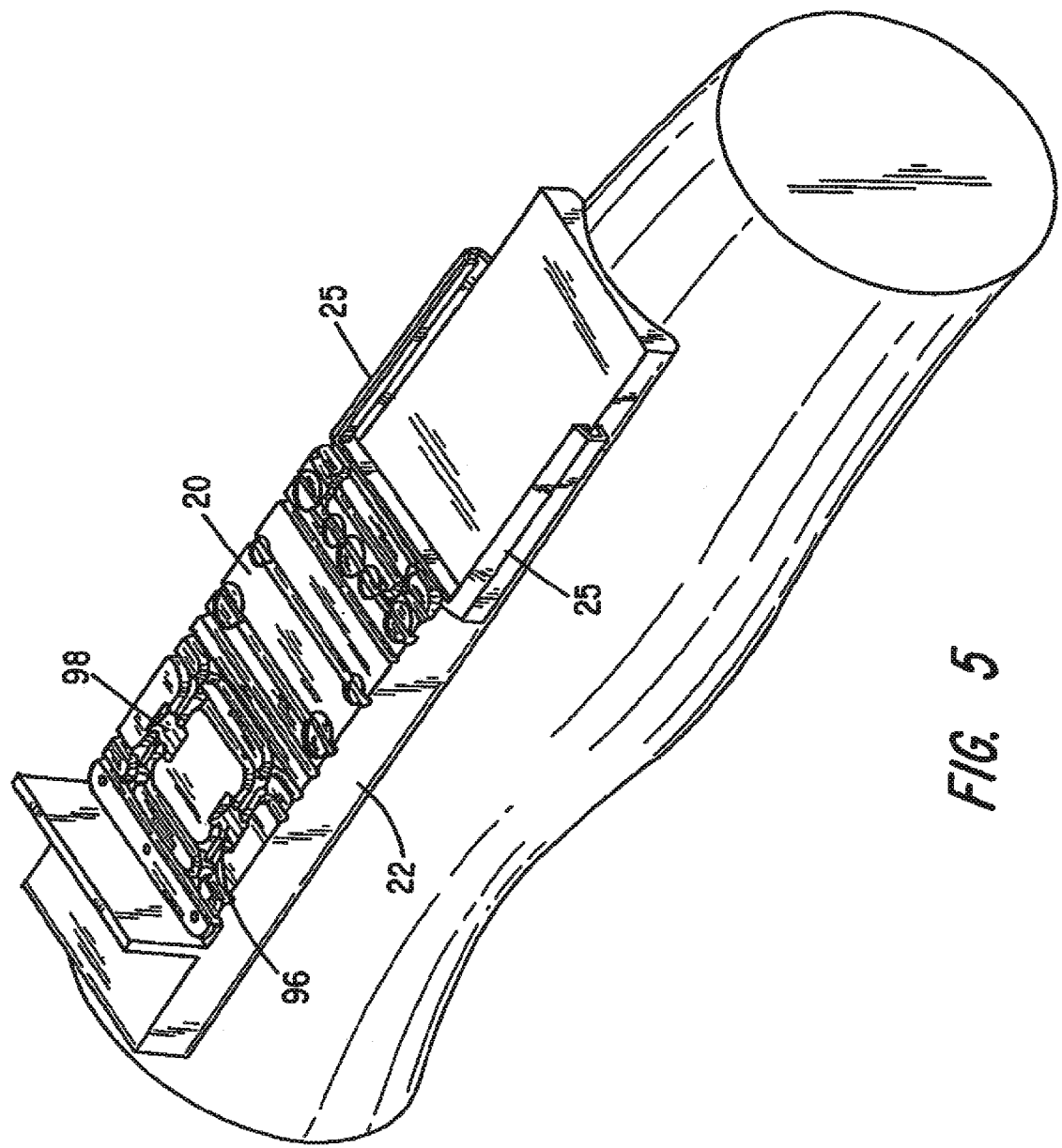
FIG. 5 is a view of the device taken with the top end plate, pump frame and cartridge removed to reveal the bottom end plate configuration.
Figure 14:
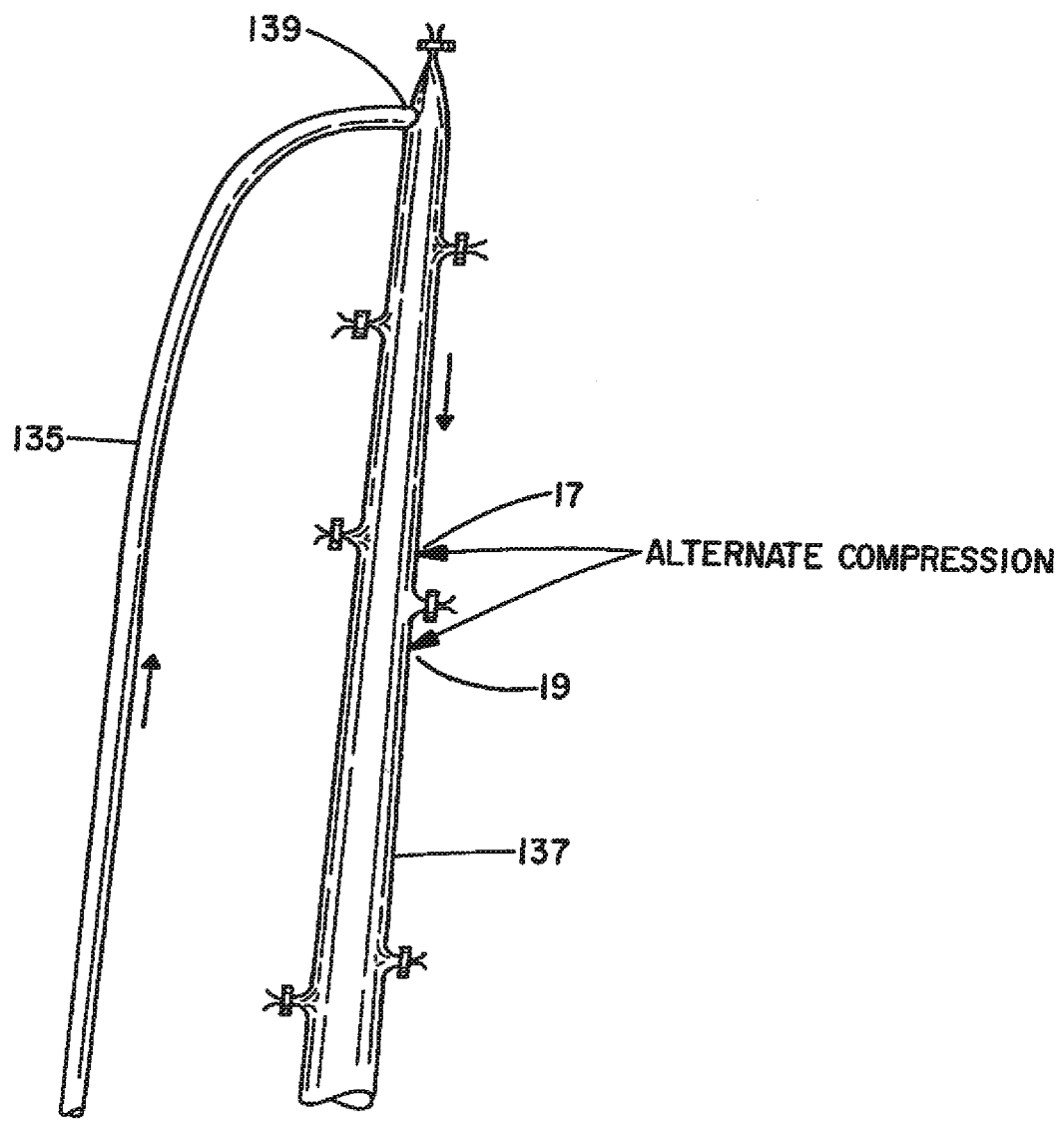
FIG. 14 is a volar view of blood vessels in the left forearm with in situ debranched vein fistula graft.

In preparing a patient for use of the wearable hemodialyzer of the present invention, a conventional, plastic tube arteriovenous fistula graft can be surgically implanted in the patient's forearm or, alternatively, and perhaps preferably, an in situ debranched vein fistula graft may be surgically created by anastomosing an artery to the debranched vein as seen in FIG. 4. Retaining its natural (vaso vasorum) blood supply, lymph drainage and nervous and elastic surround, the vein fistula graft is expected to remain especially resilient, particularly to the small cannulae required for the target 20-30 ml/min flow. In creating the in situ fistula graft, vein branchings can be ligated or stapled via minimal skin incisions, while the fistula anastomosis is being performed or subsequently in an already established fistula. Swift arterial run-off is thereby established in a single subcutaneous vein, much like correcting for downstream vein complex malfunctioning in conventional AV fistulae. When periodically compressed, the vein fistula graft repeatedly harbors arterial pressure on one side of the compression and venous pressure on the other. The sites of compression are preferably alternated acutely and shifted chronically in order to prevent surrounding tissue necrosis and intimal abrasion. In FIG. 14, numeral 135 identifies the radial artery and 137, the intermediate antebrachial vein that are anastomosed at 139.

When the fistula graft is compressed at a predetermined location thereon, the portion of the graft proximal of the compression site will be at arterial pressure and the portion of the graft distal of the compression site will be at venous pressure. When the compression is released, the whole fistula graft will be at approximately venous pressure.

As best seen in FIG. 1, the tubing segments A and A' from the upper and lower disposables 14 and 18 join together and are adapted to connect to a commercially-available double lumen needle cannula, such as available from CR Bard Corporation. The needle cannula connected to tubular segments A and A' will be inserted into the fistula graft at a location between the arterial anastomosis and the point where compression is applied to temporarily occlude the fistula graft. In a similar fashion, tubular segments D and D' on the upper and lower RF welded disposables 14 and 20 are brought together and terminate with a needle cannula that is adapted to be inserted percutaneously into the fistula graft at a location downstream of the compression point. Tubular segments K and K' that lead from the anticoagulant reservoirs 52 and 52' are joined and brought in through a hub on the arterial cannula such that the anti-coagulant will be slowly injected directly inside the tip of the inflow arterial cannula, via its second small lumen. The anticoagulant administration is proportional and appropriate for the quantity of blood flowing through the device, anticoagulating that peripheral blood flow therapeutically, while the patient is no more than prophylactically anticoagulated to a low, safe level.

The disposable, blood-contacting RF welded members 14 and 18 are preferably designed to be replaced at 3½ day intervals to inhibit infection and, more importantly, to replenish the supply of anticoagulant and calcium magnesium solution. Removal of the cannulae at 3½ day intervals should allow the in situ graft tissues to heal rapidly and without complication.

The tabs 116 and 118 of the disposables are adapted to be wrapped around the forearm and adhered to each other with Velcro fasteners thereon, thereby accommodating considerable variations in patients' anatomy. Offsets in mounted height between the two disposables assure that the dialyzers, anticoagulant and calcium magnesium reservoirs and other components will not directly overly each other, rather will nestle side-by-side, resulting in the least obtrusive space occupied around the forearm.

Figure 3:
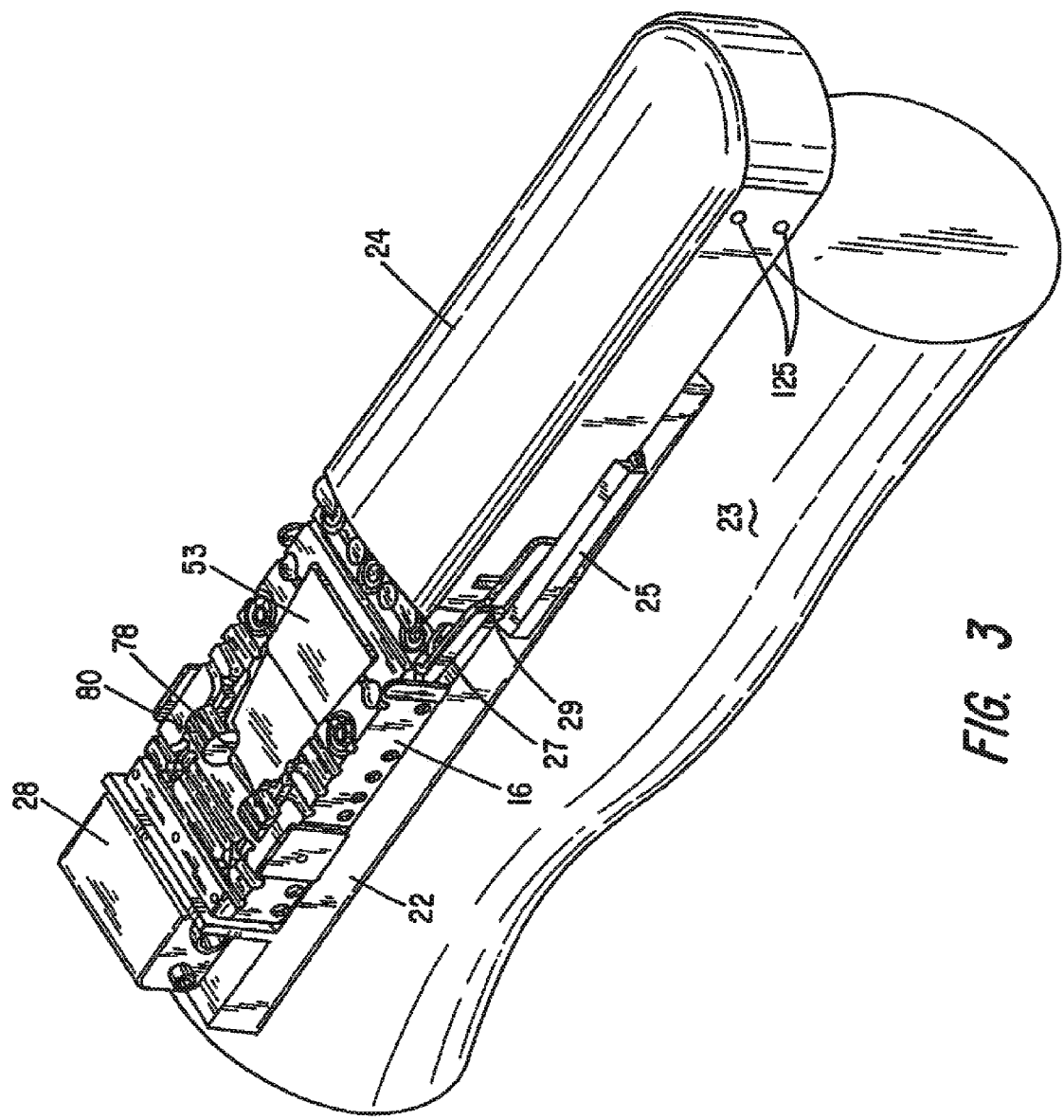
FIG. 3 is a perspective view of the device of FIG. 1 with the top end plate and disposable layers removed to reveal internal working parts thereof.

As shown in FIGS. 3 and 4, which illustrate the preferred embodiment when viewed from the patient's perspective on his/her left forearm and wrist 23, the urease and adsorbent cartridge 24/26 is adapted to slide onto the base member 22 in guide slots 25. The cartridges include quick-release clips 27 on opposed sides with integral hinges 29 to hold them in place. The several sized cartridges may be replaced every two or four hours during daytime while a larger capacity cartridge (pictured) lasting, say, eight hours may be used for nighttime application. The smaller-sized cartridges are less intrusive as far as a subject's wrist motion is concerned.

As can be seen in FIG. 2, the cartridge segments 24 and 26 include a central vertical divider 25 and a central horizontal divider 27 that divide the cartridge into two upper channels and two lower channels, the two upper channels and two lower channels being continuous, respectively, through upper and lower holes in the central vertical divider that are in line/with holes 125 in the opposed sides of the cartridge. Each of the compartments is loaded with layered urease, zirconium phosphate, hydrous zirconium oxide and activated carbon or their functional equivalent. Dialysate exiting the dialyzer 38 at port 44 travels through conduit segment E through the check valves 56, 68, 131, 129 and 127 to enter the upper left quadrant of the cartridge 24/26 at port 47 and returning via the upper right quadrant to enter the port 48 of the upper disposable where it then travels through conduit segment H and to the dialysate inlet port 46 of the cartridge 38. In a similar fashion, dialysate traversing the lower disposable member 18 flows through the lower left quadrant of the cartridge 24/26 and back through the lower right quadrant of the cartridge from the outlet ports 47' and inlet port 48' of the disposable. Any concern over how to prevent the cartridges from being inadvertently used beyond their specified time limits and eventually spilling ammonia can be resolved in a number of ways. For example, specific interlocks might initiate a timer which would alert the patient with an audible or vibratory signal. Alternatively an ameroid, which is a plastic material that swells over time in an aqueous medium, could be included in the flow path of each cartridge in the form of a small sphere that would occlude the duct from within around the time that the cartridge would be expected to become exhausted.

A thin elastic bladder-like container (not shown) can be stretched over the cartridge to encompass the outlet ports 125 to both contain necessary dialysate to fill the circuit and to permit excess dialysate to collect around the cartridge until it can be emptied in an appropriate facility. It is also contemplated that a bedside suction pump and limited sized collection bag in a vacuum chamber can be utilized to assist the removal of a predetermined, limited, volume of excess fluid while the patient is asleep.

The top end plate 12 and the bottom end plate 20 each have a pattern of grooves formed inward that when placed in registration with the frame member 16 create channels for receiving segments of the fluid carrying conduits on the upper and lower RF sealed disposables 14 and 18 without distorting, i.e., closing the fluid flow paths. FIG. 6 clearly shows the groove pattern on the upper surface of the bottom end plate 20 and this pattern is replicated on the lower surface of the top end plate 12.

The lower RF sealed blood contacting disposable 18 differs from the upper one 14 in only two small ways. The lower disposable 18 has its parallel anticoagulant and CaMg ducts located more to the left while the corresponding ducts on the upper disposable 14 are more to the right when viewed in FIGS. 7 and 8. This difference is to accommodate their being acted upon by the left-hand roller pump 78 in the case of the lower disposable 18 and by the right-hand roller pump 80 in the case of the upper disposable 14. In this fashion, anticoagulant from the reservoirs 52 and 52 is propelled toward the tip of the arterial cannula and CaMg from the reservoirs 54 and 54' toward the dialysate inflows of the dialyzers 38 and 38'. Another slight difference results from the two disposables occupying mirror image locations in the composite device. The blood and major dialysate ventricles 50, 50' and 42, 42' protrude toward the center and into the opening 62 of the frame member 16. In that they protrude from opposite directions, they interact with the lever 53 that lies between them. The opposite side of each major ventricle is supported by the flat surfaces of the top and bottom end plates 12 and 20 preventing bulging of the ventricles in a direction other than toward the center of the device.

Operation

Having described the mechanical construction of the continuously wearable hemodialyzer comprising a preferred embodiment, consideration will next be given to its mode of operation. In this regard, let it be assumed that a cycle has just been completed in which arterial engorgement of the ventricle 50 on the upper disposable 14 has driven the lever 53 to its lowermost disposition within the frame 16. The electronic control circuit of FIG. 10 outputs as pulse to activate a means, such as a motor-driven pair of spaced-apart cams mounted on the opposite (volar) side of the forearm on which the hemodialyzer 10 is mounted. The cam is positioned so as to compress the fistula graft to thereby establish an arterial/venous pressure differential in the graft. Rather than a motor driven cam for applying compression to the fistula graft at locations 17 and 19 in FIG. 14, a pair of solenoids or plungers driven by a $CO_2$ cartridge might also be used, At this time, the permanent magnet 104 (FIG. 9) is being attracted to the lower electromagnet 34 while the permanent magnet 106 is being repelled by it. The movement of the permanent magnet 104 against a knife edge on conduit segment C on the lower disposable 18 results in a filling of the lower blood ventricle 50'. At the same time, the permanent magnet 106 is being attracted by the electromagnet 30 against the inflow C of the upper blood ventricle 50 while the outflow therefrom has become unoccluded.

As a result, the lever plate 53 is driven upward as the blood ventricle 50' is being filled with blood under arterial pressure. The movement of the lever plate against the upper blood ventricle 50 directs its blood through the upper dialyzer 38 and back into the downstream segment of the fistula graft which is at a venous pressure. At the same time, the contents of the upper dialysate ventricle 42 is squeezed out to flow through the one-way valves 58, 131, 129 and 127 and into the upper left quadrant of cartridge 24/26.

As the lever plate 53 rises, it drives one of the roller pumps 80 to cause anti-coagulant to be injected into the tip of the arterial catheter and CaMg solution into the inflow of the dialyzer 38, respectively.

Also, as the lever plate 53 is driven upward, the Hall sensor in the frame 16 senses the passage of a small permanent magnet mounted to the lever plate causing a reversal in the polarity of the electromagnets preliminary to a subsequent pass of the lever plate 53 in a downward direction.

A DC electrical impulse from the control circuit of FIG. 10, at the same or multiple interval, results in the application of pressure to the fistula graft at a location offset from the previous point of compression. With the subcutaneous fistula graft again compressed, arterial/venous pressure differential is again created in the graft. The reversal of polarity of the permanent magnets results in a blocking of the outflow from the blood ventricle 50 of the upper disposable member of FIG. 8 while the inflow to the blood ventricle 50' on the lower disposable member of FIG. 7 becomes occluded. Thus, as the upper blood ventricle 50 is filling due to arterial pressure, it drives the lever plate 53 downward to squeeze blood from the ventricle 50' of the lower disposable 18 and back into the venous segment of the subcutaneous graft and to empty the dialysate solution from bladder 42' through the lower quadrants of the cartridge 24/26.

The downward movement of the lever plate 53 results in rotation of the opposite roller pump 78, causing anticoagulant to be injected into the tip of the arterial catheter and CaMg into the inflow of the lower dialyzer.

The downward movement of the lever plate is again sensed by the Hall sensor of the control circuit of FIG. 10 to reverse the polarity of the electromagnets and the cycle again repeats with the lever plate 53 again being driven in an upward direction.

It can be seen that the apparatus of the present invention disclosed in FIGS. 1-11 hereof and its mode of operation provide modulated active arterial-venous primary blood flow and secondary dialysate, anticoagulant and CaMg pumping utilizing the patient's own arterial/venous blood pressure differential to achieve continuous dialysis treatment in patients having failed kidney function. Dangerous mechanical pumps are avoided. Regional anticoagulation of the relatively small amount of blood flowing through the extracorporeal circuit inhibits clotting therein, but does not significantly depress systemic hemostasis, and avoids the need for dangerous anticoagulant reversing agents.

Alternative Embodiments

While the kidney dialysis design described above features both upper and lower RF sealed disposables as well as electromagnets arrayed both above and below, some advantage might be gained from eliminating the lower disposable and the lower electromagnets. Coil or other spring return would be substituted and as a result, not only would a considerable component-expense be eliminated, there would also be the opportunity to slim the profile of the system on the arm.

With only minor revisions to the disposable, flexible plastic, blood-contacting members illustrated in FIGS. 7 and 8, the device of the present invention may be adapted to function as an artificial liver until a suitable transplant becomes available, or, indeed, if none ever is found.

Failure of all of the filtration or exchange techniques resulted largely from their inability to match or even approach the efficiency of the liver in clearance function and led investigators to explore membrane limited cross circulation methods using living animals. The first use of this approach was in 1959, when Kimoto used cross-hemodialysis between human and dog to support a patient with liver failure. (Kimoto, J. "The Artificial Liver Experiments and Clinical Applications". ASAIO Trans 1959; 5:102-110.) The Kimoto device was made up of two blood-filled circuits, each containing a segment of semi permeable cellophane tubing. Both segments appear to have been immersed in the identical tank of dialysate. The patient's blood circulated through one circuit, while the dog's blood circulated through the other circuit. Dialyzable toxins from the patient purportedly crossed the cellophane segments and the dialysate and were metabolized by the dog's liver. This device was used on a 20-year-old man with severe hepatic encephalopathy. After 55 minutes of cross-hemodialysis, he regained consciousness and became lucid, but he died seven days later of cardiac failure. However, this case may have demonstrated that membrane limited cross-circulation with a xenogeneic liver could provide short-term hepatic support.

Figure 11:
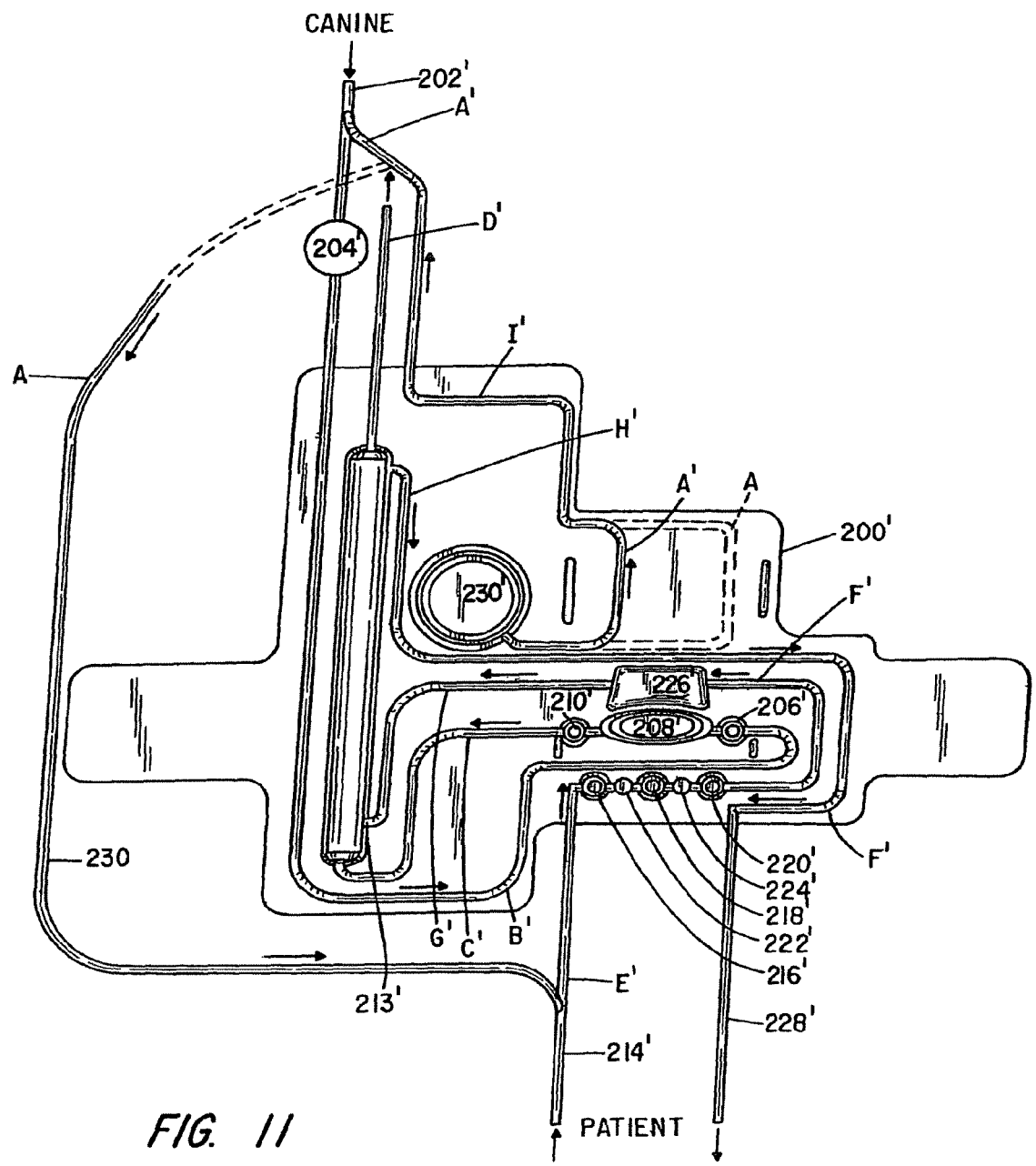
FIG. 11 is a plan view of an alternative lower disposable blood co-acting layer when implementing an artificial liver.

Referring to FIG. 11, it shows the configuration of the upper and lower disposables that are substituted for those of FIGS. 7 and 8 in implementing an artificial liver. Like the artificial kidney previously described, the upper and lower disposables differ in the location of the tubing segments A and A' with the tubing segment on the upper disposable A located so as to be operated upon by the caged roller assembly 80 of FIG. 9 and the tubing segment of the lower disposable A' operated upon by the cage roller assembly 78 in FIG. 9. Unlike the artificial kidney, where A and A' join together to inject anticoagulant almost continuously into the patient's arterial cannula which is located at the top of the kidney drawing of FIG. 7, in the liver embodiment of FIG. 11, tubing segment A' is shown being directed at the canine arterial cannula and tubing segment A is directed at the patient's arterial cannula.

Also unlike and in reverse from the kidney, the patient's arterial blood pressure containing ventricles 226, 226' and associated electromagnets and permanent magnet occluders are located closer to the fulcrum 84 of the swinging lever 53 than are the dog's ventricles 208, 208' and their passive check valves. This constitutes one of several strategies employed to assure that the dog's blood can never achieve a higher pressure than the patient's blood. One would wish to assure that there can never be contamination of the patient with dog's blood, even in case of a broken fiber. One would thereby avoid any likelihood of a patient vs. dog's blood allergic reaction. Other features employed in the artificial liver embodiment toward the same purpose of assuring that dog's blood is unlikely to ever contaminate patient's blood include: lining only veno venous cannulation of the dog's fistula graft without compression-arterialization. While the dog's blood ventricles 208, 208' are now located further from the fulcrum 84, they are capable of pumping their circuits, the dog's ventricles filling pressure being supplied by attaching the artificial liver apparatus onto the dog's harness where the dog's venous pressure (and gravity) can distend those relaxed ventricles.

The dog has been provided a compressible, but in this case non-compressed, arterial venous fistula graft in a pedicle of skin around the back of the neck that is adapted to be accessed by needle cannulae (not shown) coupled to the tubing segment 202' so that blood can be made to flow through a future antigen filter 204° and the tubing segment B' formed between the RF welded layers comprising the disposable 200'. The tubing segment B' is shown as leading to a first passive check valve 206', a dog's blood inflatable ventricle 208' and a second passive check valve 210' connected by tubing segment C' to an inlet of an exchanger 212' similar in construction to the dialyzer 38 of the kidney embodiment in that it contains a large plurality of tubules comprising semi-permeable membranes. Appropriate manifolds are provided so that the dog's blood entering the exchanger 212' from the tubing segment C' is made to flow through the plurality of lumens of the tubules before exiting the exchanger via tubing segment D' that leads to a needle cannula (not shown) in the fistula graft preferably located in the dog's neck.

Plastic tubing 214' connects to a needle-cannula (not shown) insertable into an arterial venous fistula graft in the patient's arm and connects to a tubing segment E' formed in the disposable 200'. Connected in series with tubing segment E' are one-way valves 216', 218' and 220' which, together with compressible bladders 222' and 224', form an auxiliary pump for possibly moving patient's arterial blood through a tubing segment F' to a patient's blood ventricle 226', still another way to assure that the patient's blood will be at a higher pressure than the animal's. The inflatable, compressible ventricle 226' is then connected via tubing segment G' formed in the disposable 200' leading to the patient's blood inlet 213' of the membrane exchanger 212'. The patient's blood flows over the outer surface of the tubules through which the dog's blood is made to pass.

The patient's blood exits the exchanger 212' by way of a tubing segment H' that is traceable back to an external plastic tube 228° leading to a needle cannula insertable into the fistula graft, downstream from the patient's fistula graft compressors, at a point exposed to venous pressure.

Formed between the layers comprising the laminated structure of the disposable 200' is a reservoir 230' that contains an anticoagulant, such as heparin, possibly preserved in a crushable ampule. The pumping action afforded by inflation and deflation of the ventricles 226, 226° acting on the lever plate 53 and the roller pumps (FIG. 9) measures out metered quantities of heparin, via tubing segments A and A' (A segment being on the upper disposable and segment A' being on the lower disposable). A' leads from the lower disposable to the cannula placed in the dog's fistula graft. Flexible tube A leads back from the upper disposable and joins the needle cannula insertable in the arterial portion of the patient's fistula graft.

Recalling from the description of the artificial kidney embodiment how the non-disposable pump structure cooperates with the upper and lower disposable members through appropriate energization of the electromagnets. The human blood inflow occluder (not shown) related to patient's ventricle 226 on the upper liver disposable is made to open while the (identical) human blood inflow occluder on the lower disposable becomes closed. Simultaneously, the human blood outflow occluder (not shown) on the upper disposable becomes closed while the (identical) human blood flow occluder on the lower disposable becomes open. The upper human blood ventricle 226, therefore, begins to fill and to displace the lever plate 53 downward to press against the corresponding human blood ventricle 226', emptying both it and the lower dog's blood ventricle 208' via passive in and out check valves 206' and 210'. The dog's blood is emptied through the fibers of dialyzer 212' via tubing segment D'.

As the lever plate 53 is driven downward, it presses on the patient's blood ventricle 226' forcing the patient's blood through the tubing segment G', and, after bathing the outside of the fibers in the dialyzer 212', out through the tubing segment H'. Slightly less efficient cocurrent flow is accepted in this case (instead of counter current flow as in the kidney embodiment) as a necessary part of the transcendent strategy to, as much as possible, maintain a higher pressure on the patient's side compared with the dog's side. Toxins present in the patient's blood pass in through the membrane walls of the hollow fibers contained within the exchanger 212' to the dog's blood and are ultimately removed therefrom by the dog's functioning liver, Similar to the case of the kidney embodiment, movement of the pump's lever plate down drives the roller pump assembly 78 in a direction to move anticoagulant from the reservoir 230' to the dog's cannula via tubing segment A'. Lever plate movement upward drives anticoagulant by means of roller pump assembly 80 from reservoir 230 of the upper disposable on through tubing segment A and into the patient's arterial cannula.

As has already been explained in connection with the artificial kidney embodiment, as the lever plate 53 is driven in one direction or the other by the filling of the human blood ventricles on the upper or lower disposables, a Hall sensor affixed to the frame senses the passage of a permanent magnet affixed to the lever plate and sends a signal to the electronic circuitry of FIG. 10 to cause a reversal in the potential polarity of the electromagnets, resulting in a shift in the filling of the human blood ventricles from the lower to the upper disposable or from the upper to the lower disposable after the next pulse of direct current.

Figure 12:
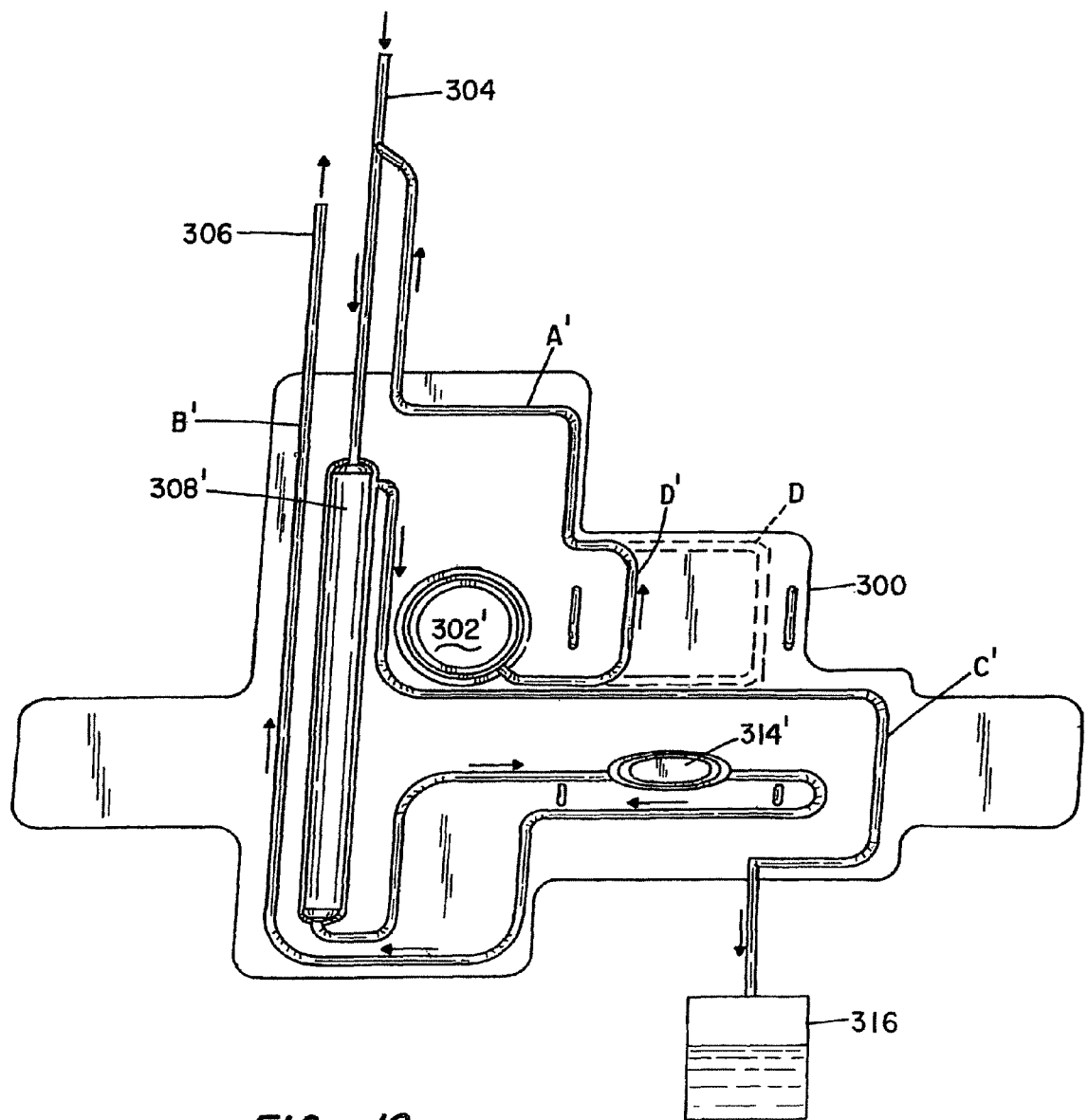
FIG. 12 is a plan view of an alternative lower disposable blood co-acting layer when implementing a device for treating Congestive Heart Failure (CHF)

FIG. 12 illustrates how the layout of the upper and lower disposable, blood-contacting members can be changed from that shown in FIGS. 7 and 8 where the apparatus of the present invention is to be used in treating congestive heart failure (CHF). CHF implies a weakening of the heart, resulting in "congestion" or backing up of blood waiting to be pumped through the lungs and around the body. Weakening of the heart might be caused by a number of immediate and remote causes. It affects nearly 5 million patients in the U.S. alone. The result in each ease is that the venous pool enlarges and tissues become "water-logged". For example, ankles swell and lungs exchange gases poorly—the classical "Dropsy". A number of medical treatments have been attempted, mostly aimed at either strengthening the heart's pumping or otherwise stimulating the kidneys to more effectively remove water from the circulation.

Often when medical or surgical efforts fail, patients die miserably of suffocation. A variety of ancillary pathologies might intervene, e.g., pneumonia. Therefore, cardiologists stealing from the nephrologists' playbook have begun intermittently "hemodiafiltering" or "hemofiltering" patients of watery solvent. This is preformed by means of either conventional hemodialysis machines or with what are, to most intents and purposes, dialysis machines retaining most of the capabilities but lacking the capacity to carry out solute exchange. The emphasis, rather, is on squeezing fluid out of blood through a semi-permeable membrane acting as a sieve. Cardiologists typically carry out such hemofiltrations at intervals suited to the individual, and they typically may remove several liters of fluid from the bloodstream and eventually from the tissues within a few hours time. This is a strenuous procedure for both patients and staff and predicatively yields limited and temporary benefits.

It would, therefore, be desirable for such hemofiltration to be carried out slowly and continuously and with much greater effect. Nearly identical apparatus as depicted in FIGS. 1-10 may, therefore, be utilized for continuous 24/7 ambulatory hemofiltration and with an even larger element of suction being utilized during recumbent night time periods to draw liquid out of the blood during sleeping hours. Referring to FIG. 12, there is shown one of the two blood-contacting, flexible plastic disposables indicated generally by numeral 300'. It has a reservoir 302' for containing a volume of an anticoagulant, perhaps in a crushable ampule for storage, that is connected by way of a tubular channel A' to a cannula 304 adapted to be inserted into a subcutaneous arterial venous fistula graft or, as in the case of the other previously described embodiments, into an In Situ Debranched Vein Fistula Graft (VFG) upstream of a graft compression site. A second cannula 306 is connected to a tubular passage B' formed between the two layers of laminated plastic comprising the disposable 300'. Arterial blood is made to flow through a dialyzing cartridge 308' supported on the disposable 300' so as to flow through the large plurality of tubules contained within the dialyzer 308'.

As with the earlier described embodiments, under control of magnetically-actuated occluders, blood is made to fill and empty from an expandable ventricle 314'. Excess water in the blood passes through the walls of the semi-permeable membranes comprising the tubules within the cartridge 308' and are allowed to flow through tubing segment C' to a common collection bag 316.

As the reader will understand from the previously described embodiments, permanent magnet occluders attracted and repelled by electromagnets selectively occlude and unocclude the ducts leading to and from the two blood ventricles 314 and 314' on the corresponding upper and lower disposables. Physically, the lower and upper disposables differ only in the location of the tubular segments identified as D' and D where segment D' is on the lower disposable and segment D is on the upper disposable.

When the lower and upper disposables are positioned as shown in the exploded view of FIG. 2, one of the cage roller assemblies 78 or 80 will cooperate with segment D' and the other with the segment D. The blood expandable ventricle 314', when filling, serves to displace the lever plate 53 so as to press against the corresponding ventricle on the upper disposable member causing it to empty while, at the same time, rotating one of the roller pump assemblies in a direction to pump anti-coagulant, possibly contained for storage in a sealed in crushable ampule, from the reservoir 302'. When the associated electromagnets reverse polarity, the blood expandable bladder on the upper disposable begins to fill, moving the lever plate 53 downward to compress and empty the ventricle 314' and, at the same time, peristalticly pumping anticoagulant from the reservoir on the upper disposable corresponding to reservoir 302' on the lower disposable through tubing segments and A to exit the cannula 304 and preventing blood coagulation within the cannula.

The cyclic filling and emptying of the ventricle 314' on the lower disposable and the corresponding one on the upper disposable 314 causes the lever plate 53 to oscillate back and forth and thereby rotate the cage wheel assemblies to pump anti-coagulant in very small quantities during each stroke. The blood flowing through the filter 308' and the corresponding one 308 on the upper disposable extracts excess water from the blood, emptying it into the collection vessel 316 where it can be periodically emptied by suction or otherwise.

A third alternative embodiment illustrates the manner which the present invention can be adapted to administration of insulin to a patient suffering from insulin dependent diabetes. Insulin dependent diabetes is related to decreased production of insulin by the Islets of Langerhans cells of the pancreas. Diabetes, in both its Type I and Type II manifestations, has long been treated with insulin or insulin-like substances. Diabetes is notorious because of the dangers of unregulated blood sugar causing immediate death or harm to a wide variety of vital body systems—peripheral vascular, eyes, kidneys, etc.

To directly diagnose and treat blood, rather than subcutaneous tissue, temporary needles-catheters may have to be inserted into a vein, with ongoing threats of infection and thrombosis, especially in infection prone diabetics. Thrombosis might occur he veins or it might clog the needles being utilized for sampling. Frequent or continuous sampling, as would be required for instant feedback control, would require return of blood samples to the circulation and the blood could not be permitted to clot in the external system. Total therapeutic level anticoagulation would be required in the extracorporeal circuit. At least prophylactic anticoagulation might also be desirable in the patient, which, as has been described herein, is routinely implemented by the apparatus of the present invention. A truly intravascular glucose sensor on the end of a needle cannula would thus seem desirable, but could pose its own problems interacting with the blood. Such miniaturization would produce its own difficulties. Furthermore, without a fistula or fistula graft of some kind, the limited number of prominent naturally available veins would be unlikely to weather a lifetime of needle perforations and continuously indwelling catheters.

The present invention offers a practical alternative. It utilizes a new blood access system to resolve the conundrum without enduring the special problems of a totally implantable meter/pump feedback system. It provides the same advantages by means of the In Situ Debranched Vein Fistula Graft VFG and slight modifications of the standard wrist and forearm worn device described herein. As already explained, the VFG permits ready access to the arterial venous pressure differential simply by alternatively compressing it from without at two adjacent sites, resulting in arterial pressure upstream and venous pressure downstream from the point of transcutaneous compression. The device not only mediates the compressions, it also utilizes the arterial venous pressure differential obtained in order to modulate blood flow through the device and dispense anticoagulant into the entire extracorporeal circuit. Modulation of blood flow is to a low but adequate level for the task, e.g., 20-30 ml/min. in the case of the artificial kidney, and probably even less in the case of diabetes care where full therapeutic levels of anticoagulation can be achieved in the extracorporeal circuit without beginning to threaten the whole patient with more than prophylactic levels of anticoagulation.

As those skilled in the art can appreciate from a reading of the present specification, the VFG holds considerable advantage over alternative blood access arrangements. It does not require repeated cannulizations of centrally leading arteries and/or veins where even a single untoward event might impair an important segment of the vascular system and even threaten the life of the patient. Plastic AV fistula grafts are notorious for infection, calcification, distal anastomosis narrowing and thrombosis. Direct fistulae do not offer arterial venous pressure differential and, interestingly, when plagued with various and multiple downstream venous thromboses, are routinely convened to a single vessel "VFG" through multiple ligations of vein branches. The VFG has no downstream anastomosis. Remaining in situ, it retains its own vasavasorum and lymphatic and nerve connections, making it more resistant to infection and capable of rapid healing from day one, especially from penetrations by the small needles-cannulae required for these very low blood flows.

The blood is easily diverted from the arterialized segment of the VFG upstream from the compression location and anticoagulated to therapeutic levels from the very tip of the cannula through a second lumen extruded in the cannula or a hollow fiber laid within the blood lumen. The arterial blood then flows directly to the modulating ventricle which regulates the extracorporeal flow to the desired rate, utilizing reciprocating volumetric means. Thereafter, the blood is returned by the venous cannula to the downstream segment of the VFG. The reciprocations of the swinging lever plate also drive the miniature roller peristaltic pumps and the anticoagulant along with it. Arterial blood glucose can be continuously monitored upstream in the device and, through an electronic feedback control loop, appropriate rapid-acting (regular) insulin can be added downstream in the case of hyperglycemia, with perhaps a requirement for more than one reading and some "gradularity" built in to prevent over-reaction and swings of the glucose level up and down. Glucose might alternatively be administered, to rapidly, but not too rapidly, correct for hypoglycemia. The objective of this alternative embodiment of the invention is to conveniently place a lock on the blood glucose level for the balance of a patient's lifetime, in order to avoid the possibly immediate lethal effects of hypoglycemia as well as the chronically disastrous debilitating effects of hyperglycemia. It is expected to be especially applicable to the large proportion of diabetic patients already on dialysis, whose renal failure derives directly from their diabetes. Two therapies can easily be combined into one by including an external glucose meter, electronic feedback loop and external insulin pump directly onto the Wrist and Forearm Wearable Artificial Kidney previously described.

Figure 13:
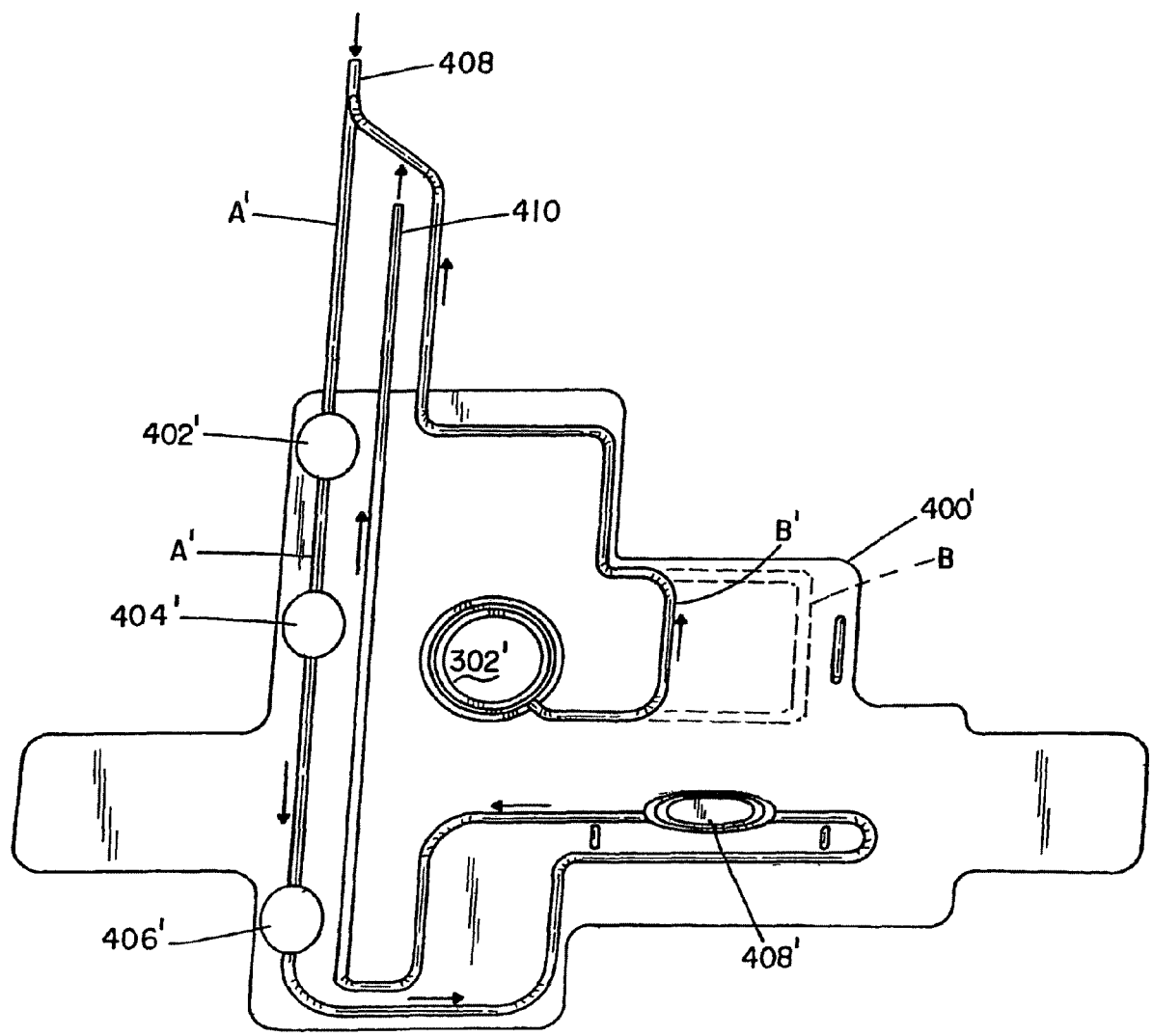
FIG. 13 is a plan view of an alternative lower disposable blood co-acting layer when implementing an artificial pancreas diabetes control.

In FIG. 13 there is shown the configuration of a lower disposable 400 in solid line and the change to the lower disposable to create the upper disposable in phantom line. The two are to be used with the non-disposable pump structure shown in FIG. 9 for use in addressing diabetes. Supported on the forearm worn assembly is a blood glucose sensor 402', an insulin pump 404' and a glucose pump 406'. The glucose sensor 402' is exposed to the patient's blood in that the percutaneous cannula 408 is adapted to pierce the arterialised side of the VFG created in the diabetic patient's arm. It is further contemplated that the output signal from the glucose sensor 402' would be utilized by an insulin pump 404' which, in turn, will inject insulin into the blood flowing through the tube segment B' in an amount based on the glucose sensor output. Likewise, the glucose pump 406' might be used to increase the level of glucose in those patients threatened by hypoglycemia. Blood is returned to the patient downstream from the compressions through A' and venous cannula 410.

As in the earlier described embodiments, flow of blood into and from the expansible ventricle 408° on the lower disposable 400' and the corresponding expansible ventricle located on the upper disposable member (not shown but substantially identical to disposable member 400') is by way of magnetically actuated occluders as more particularly described in connection with the artificial kidney embodiment of FIGS. 1-10. As in the previous embodiments, the filling of the ventricle 408' with the patient's arterial blood pivots the lever plate 53 upward against the corresponding blood filled ventricle 408 on the upper disposable which is thus emptied. As the lever plate is driven upward, it operates to rotate the roller pump assembly pressing on the tubular segment B where segment B is on the upper disposable and segment B' is on the lower disposable. The rolling movement of the roller cages on the segments B' and B function as peristaltic pumps to move an anti-coagulant to the arterial cannula 408 to maintain it and the entire device free of clotting blood.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself. For example, the invention is readily adaptable to a wide variety of excorporeal blood treatments.

What is claimed is:

1. A method for obtaining access to a patient's arteriovenous pressure differential for extracorporeal blood flow comprising the steps of:
    (a) selecting a venous segment in the patient's forearm and transecting and occluding the distal end thereof;
    (b) anastomosing a remaining end portion of the transected vein to a selected artery in the patient's forearm, creating a fistula;
    (c) debranching the selected venous segment;
    (d) inserting a first needle cannula percutaneously into the debranched vein segment for accessing AV pressure differential and extracorporeal blood flow and inserting a second needle cannula percutaneously into the debranched vein for return of the extracorporeal blood flow to the patient's circulation; and
    (e) sequentially applying and removing compression to the forearm between the first and second needle cannulae sufficient to substantially occlude blood flow through the debranched vein segment during the compression and thereby establishing the pressure differential in that when the compression is being applied, the first needle cannula is exposed to arterial pressure and when released, the first and second needle cannulae are exposed to venous pressure.

* * * * *